(12) United States Patent
Miesel et al.

(10) Patent No.: US 7,881,798 B2
(45) Date of Patent: Feb. 1, 2011

(54) CONTROLLING THERAPY BASED ON SLEEP QUALITY

(75) Inventors: Keith A. Miesel, St. Paul, MN (US); Kenneth T. Heruth, Edina, MN (US); Jonathan C. Werder, Corcoran, MN (US); Steve R. LaPorte, San Antonio, TX (US); Nina M. Graves, Minnetonka, MN (US)

(73) Assignee: Medtronic Inc., Minneapolis, MN (US)

( * ) Notice: Subject to any disclaimer, the term of this patent is extended or adjusted under 35 U.S.C. 154(b) by 826 days.

(21) Appl. No.: 11/691,430

(22) Filed: Mar. 26, 2007

(65) Prior Publication Data

US 2008/0071327 A1   Mar. 20, 2008

Related U.S. Application Data

(63) Continuation-in-part of application No. 11/081,155, filed on Mar. 16, 2005, now Pat. No. 7,590,455, which is a continuation-in-part of application No. 10/825,953, filed on Apr. 15, 2004, now Pat. No. 7,366,572, application No. 11/691,430, filed on Mar. 26, 2007.

(60) Provisional application No. 60/553,777, filed on Mar. 16, 2004, provisional application No. 60/785,819, filed on Mar. 24, 2006.

(51) Int. Cl.
*A61N 1/18* (2006.01)

(52) U.S. Cl. .......................................... 607/48; 607/26

(58) Field of Classification Search .................. 607/2, 607/3, 45, 116
See application file for complete search history.

(56) References Cited

U.S. PATENT DOCUMENTS 4,297,685 A   10/1981   Brainard, II
4,550,736 A   11/1985   Broughton et al.

(Continued)

FOREIGN PATENT DOCUMENTS

DE   198 31 109   1/2000

(Continued)

OTHER PUBLICATIONS

Office Action dated Nov. 6, 2008 for U.S. Appl. No. 11/081,857 (8 pgs.).

(Continued)

*Primary Examiner*—Carl H Layno
*Assistant Examiner*—Brian T Gedeon
(74) *Attorney, Agent, or Firm*—Shumaker & Sieffert, P.A.

(57) ABSTRACT

A medical device, such as an implantable medical device (IMD), determines values for one or more metrics that indicate the quality of a patient's sleep, and controls delivery of a therapy based on the sleep quality metric values. For example, the medical device may compare a sleep quality metric value with one or more threshold values, and adjust the therapy based on the comparison. In some embodiments, the medical device adjusts the intensity of therapy based on the comparison, e.g., increases the therapy intensity when the comparison indicates that the patient's sleep quality is poor. In some embodiments, the medical device automatically selects one of a plurality of therapy parameter set available for use in delivering therapy based on a comparison sleep quality metric values associated with respective therapy parameter sets within the plurality of available therapy parameter sets.

24 Claims, 12 Drawing Sheets

U.S. PATENT DOCUMENTS

| | | |
|---|---|---|
| 4,771,780 A | 9/1988 | Sholder |
| 4,776,345 A | 10/1988 | Cohen et al. |
| 4,846,195 A | 7/1989 | Alt |
| 5,040,536 A | 8/1991 | Riff |
| 5,058,584 A | 10/1991 | Bourgeois |
| 5,125,412 A | 6/1992 | Thornton |
| 5,154,180 A | 10/1992 | Blanchet et al. |
| 5,233,984 A | 8/1993 | Thompson |
| 5,275,159 A | 1/1994 | Griebel |
| 5,335,657 A | 8/1994 | Terry, Jr. et al. |
| 5,337,758 A | 8/1994 | Moore et al. |
| 5,342,409 A | 8/1994 | Mullett |
| 5,469,861 A | 11/1995 | Piscopo et al. |
| 5,476,483 A | 12/1995 | Bornzin et al. |
| 5,514,162 A | 5/1996 | Bornzin et al. |
| 5,593,431 A | 1/1997 | Sheldon |
| 5,622,428 A | 4/1997 | Bonnet |
| 5,645,053 A | 7/1997 | Remmers et al. |
| 5,732,696 A | 3/1998 | Rapoport et al. |
| 5,782,884 A | 7/1998 | Stotts et al. |
| 5,895,371 A | 4/1999 | Levitas et al. |
| 5,904,708 A | 5/1999 | Goedeke |
| 5,919,149 A | 7/1999 | Allum |
| 5,941,906 A | 8/1999 | Barreras, Sr. et al. |
| 5,944,680 A | 8/1999 | Christopherson et al. |
| 6,044,297 A | 3/2000 | Sheldon et al. |
| 6,045,513 A | 4/2000 | Stone et al. |
| 6,059,576 A | 5/2000 | Brann |
| 6,091,973 A | 7/2000 | Colla et al. |
| 6,095,991 A | 8/2000 | Krausman et al. |
| 6,102,874 A | 8/2000 | Stone et al. |
| 6,120,467 A | 9/2000 | Schallhorn |
| 6,128,534 A | 10/2000 | Park et al. |
| 6,157,857 A | 12/2000 | Dimpfel |
| 6,165,143 A | 12/2000 | van Lummel |
| 6,259,948 B1 | 7/2001 | Florio et al. |
| 6,273,856 B1 | 8/2001 | Sun et al. |
| 6,280,409 B1 | 8/2001 | Stone et al. |
| 6,296,606 B1 | 10/2001 | Goldberg et al. |
| 6,308,098 B1 | 10/2001 | Meyer |
| 6,315,740 B1 | 11/2001 | Singh |
| 6,351,672 B1 | 2/2002 | Park et al. |
| 6,366,813 B1 | 4/2002 | DiLorenzo |
| 6,416,471 B1 | 7/2002 | Kumar et al. |
| 6,440,090 B1 | 8/2002 | Schallhorn |
| 6,449,508 B1 | 9/2002 | Sheldon et al. |
| 6,459,934 B1 | 10/2002 | Kadhiresan |
| 6,466,821 B1 | 10/2002 | Pianca et al. |
| 6,468,234 B1 | 10/2002 | Van der Loos et al. |
| 6,514,218 B2 | 2/2003 | Yamamoto |
| 6,539,249 B1 | 3/2003 | Kadhiresan et al. |
| 6,574,507 B1 | 6/2003 | Bonnet |
| 6,605,038 B1 | 8/2003 | Teller et al. |
| 6,611,783 B2 | 8/2003 | Kelly, Jr. et al. |
| 6,659,968 B1 | 12/2003 | McClure |
| 6,687,538 B1 | 2/2004 | Hrdlicka et al. |
| 6,731,984 B2 | 5/2004 | Cho et al. |
| 6,752,766 B2 | 6/2004 | Kowallik et al. |
| 6,773,404 B2 | 8/2004 | Poezevera et al. |
| 6,819,956 B2 | 11/2004 | DiLorenzo |
| 6,878,121 B2 | 4/2005 | Krausman et al. |
| 6,881,192 B1 | 4/2005 | Park |
| 6,884,596 B2 | 4/2005 | Civelli et al. |
| 6,890,306 B2 | 5/2005 | Poezevera |
| 6,928,324 B2 | 8/2005 | Park et al. |
| 6,964,641 B2 | 11/2005 | Cho et al. |
| 7,146,211 B2 | 12/2006 | Frei et al. |
| 7,162,304 B1 | 1/2007 | Bradley |
| 7,209,787 B2 | 4/2007 | DiLorenzo |
| 2001/0037067 A1 | 11/2001 | Tchou et al. |
| 2002/0077562 A1 | 6/2002 | Kalgren et al. |
| 2002/0091308 A1 | 7/2002 | Kipshidze et al. |
| 2002/0161412 A1 | 10/2002 | Sun et al. |
| 2002/0169485 A1 | 11/2002 | Pless et al. |
| 2002/0177882 A1 | 11/2002 | DiLorenzo |
| 2002/0193697 A1 | 12/2002 | Cho et al. |
| 2002/0193839 A1 | 12/2002 | Cho et al. |
| 2003/0004423 A1 | 1/2003 | Lavie et al. |
| 2003/0139692 A1 | 7/2003 | Barrey et al. |
| 2003/0149457 A1 | 8/2003 | Tcheng et al. |
| 2003/0153953 A1 | 8/2003 | Park et al. |
| 2003/0153955 A1 | 8/2003 | Park et al. |
| 2003/0153956 A1 | 8/2003 | Park et al. |
| 2003/0163059 A1 | 8/2003 | Poezevera et al. |
| 2003/0171791 A1 | 9/2003 | KenKnight et al. |
| 2003/0195588 A1 | 10/2003 | Fischell et al. |
| 2003/0212445 A1 | 11/2003 | Weinberg |
| 2004/0002741 A1 | 1/2004 | Weinberg |
| 2004/0002742 A1 | 1/2004 | Florio |
| 2004/0015103 A1 | 1/2004 | Aminian et al. |
| 2004/0049132 A1 | 3/2004 | Barron et al. |
| 2004/0102814 A1 | 5/2004 | Sorensen et al. |
| 2004/0111040 A1 | 6/2004 | Ni et al. |
| 2004/0111041 A1 | 6/2004 | Ni et al. |
| 2005/0021103 A1 | 1/2005 | DiLorenzo |
| 2005/0021104 A1 | 1/2005 | DiLorenzo |
| 2005/0039745 A1 | 2/2005 | Stahmann et al. |
| 2005/0042589 A1 | 2/2005 | Hatlestad et al. |
| 2005/0061320 A1 | 3/2005 | Lee et al. |
| 2005/0065560 A1 | 3/2005 | Lee et al. |
| 2005/0076908 A1 | 4/2005 | Lee et al. |
| 2005/0085738 A1 | 4/2005 | Stahmann et al. |
| 2005/0113710 A1 | 5/2005 | Stahmann et al. |
| 2005/0119703 A1 | 6/2005 | DiLorenzo |
| 2005/0143617 A1 | 6/2005 | Auphan |
| 2005/0177192 A1 | 8/2005 | Rezai et al. |
| 2005/0209511 A1 | 9/2005 | Heruth et al. |
| 2005/0209512 A1 | 9/2005 | Heruth et al. |
| 2005/0209513 A1 | 9/2005 | Heruth et al. |
| 2005/0209643 A1 | 9/2005 | Heruth et al. |
| 2005/0209644 A1 | 9/2005 | Heruth et al. |
| 2005/0209645 A1 | 9/2005 | Heruth et al. |
| 2005/0215847 A1 | 9/2005 | Heruth et al. |
| 2005/0215947 A1 | 9/2005 | Heruth et al. |
| 2005/0216064 A1 | 9/2005 | Heruth et al. |
| 2005/0222522 A1 | 10/2005 | Heruth et al. |
| 2005/0222626 A1 | 10/2005 | DiLorenzo |
| 2005/0222643 A1 | 10/2005 | Heruth et al. |
| 2005/0234514 A1 | 10/2005 | Heruth et al. |
| 2005/0234518 A1 | 10/2005 | Heruth et al. |
| 2005/0240086 A1 | 10/2005 | Akay |
| 2005/0240242 A1 | 10/2005 | DiLorenzo |
| 2005/0245790 A1 | 11/2005 | Bergfalk et al. |
| 2005/0245988 A1 | 11/2005 | Miesel |
| 2006/0224191 A1 | 10/2006 | Dilorenzo |
| 2006/0293720 A1 | 12/2006 | DiLorenzo |
| 2007/0073355 A1 | 3/2007 | Dilorenzo |
| 2007/0142862 A1 | 6/2007 | Dilorenzo |

FOREIGN PATENT DOCUMENTS

| | | |
|---|---|---|
| DE | 100 24 103 | 11/2001 |
| EP | 0 564 803 A1 | 10/1993 |
| EP | 0 849 715 B1 | 6/1998 |
| EP | 1 195 139 A1 | 4/2002 |
| EP | 1 291 036 A2 | 3/2003 |
| EP | 1 308 182 A2 | 5/2003 |
| EP | 1 437 159 A1 | 7/2004 |
| EP | 1 322 227 B1 | 12/2005 |
| GB | 2 330 912 A | 5/1999 |
| WO | WO 98/00197 | 1/1998 |
| WO | WO 99/13765 | 3/1999 |
| WO | WO 01/37930 | 5/2001 |
| WO | WO 02/28282 | 4/2002 |

| | | |
|---|---|---|
| WO | WO 02/41771 | 5/2002 |
| WO | WO 02/087433 | 11/2002 |
| WO | WO 02/096512 | 12/2002 |
| WO | WO 02/100267 | 12/2002 |
| WO | WO 03/024325 | 3/2003 |
| WO | WO 03/051356 | 6/2003 |
| WO | WO 03/065891 | 8/2003 |
| WO | WO 2005/028029 | 3/2005 |
| WO | WO 2005/035050 | 4/2005 |

OTHER PUBLICATIONS

Response dated Jan. 6, 2009 for U.S. Appl. No. 11/081,857 (6 pgs.).
Response dated Feb. 12, 2009 for U.S. Appl. No. 11/081,155 (7 pgs.).
Office Action dated Dec. 12, 2008 for U.S. Appl. No. 11/081,811 (12 pgs.).
Responsive Amendment dated Mar. 12, 2009 for U.S. Appl. No. 11/081,811 (13 pgs.).
Office Action dated Oct. 16, 2007 for U.S. Appl. No. 10/826,925 (29 pgs.).
Response to Office Action dated Jan. 16, 2008 for U.S. Appl. No. 10/826,925 (20 pgs.).
Office Action dated May 5, 2008 for U.S. Appl. No. 10/826,925 (12 pgs.).
Office Action dated May 30, 2008 for U.S. Appl. No. 11/081,811 (13 pgs.).
Office Action dated May 6, 2008 for U.S. Appl. No. 10/825,955 (13 pgs. ).
Response to Office Action dated Jul. 2, 2008 for U.S. Appl. No. 10/825,955 (13 pgs.).
Office Action dated May 9, 2008 for U.S. Appl. No. 11/081,857 (10 pgs.).
Office Action dated Apr. 4, 2008 for U.S. Appl. No. 11/081,155 (9 pgs. ).
Amzica, "Physiology of Sleep and Wakefulness as it Relates to the Physiology of Epilepsy," Journal of Clinical Neurophysiology, American Clinical Neurophysiology Society, 19(6), pp. 488-503, (2002).
Dinner, "Effect of Sleep on Epilepsy," Journal of Clinical Neurophysiology, American Clinical Neurophysiology Society, 19(6), pp. 504-513, (2002).
Foldvary-Schaefer, "Sleep Complaints and Epilepsy: The Role of Seizures, Antiepileptic Drugs and Sleep Disorders," Journal of Clinical Neurophysiology, American Clinical Neurophysiology Society, 19(6), pp. 514-521, (2002).
Mendez et al. "Interactions Between Sleep and Epilepsy," Journal of Clinical Neurophysiology, American Clinical Neurophysiology Society, 18(2), pp. 106-127, (2001).
"MiniMitter® Physiological and Behavioral Monitoring for Humans and Animals," http://www.minimitter.com/Products/Actiwatch, 3 pgs. Feb. 20, 2006.
"IBM & Citzen Watch develop Linux-based 'WatchPad'," 5 pgs., http://www.linuxdevices.com/news/NS6580187845.html, Feb. 20, 2006.
"Design Competition: Runners-Up for the Best Three Designs," EPN, vol. 26, No. 1, 1 pg., (2002).
"Watch," Wildpedia, the free encyclopedia, 6 pgs., http://en.wikipedia.org/wiki/Watch, Feb. 20, 2006.
Kassam, "2005 EDP Topic 'MK4': Tremor Data-Logger for Parkinson's Disease Patients," http://www.ee.ryerson.ca/~courses/edp2005/MK4.html, 3 pgs., Feb. 20, 2006.
Tuisku, "Motor Activity Measured by Actometry in Neuropsychiatric Disorders," Department of Psychiatry, University of Helsinski, Helsinki, Finland, 115 pgs. (2002).
Smith et al., "Presleep Cognitions in Patients with Insomnia Secondary to Chronic Pain," Journal of Behavioral Medicine, vol. 24, No. 1, pp. 93-114, (2001).
Smith et al. "How do sleep disturbance and chronic pain inter-relate? Insights from the longitudinal and cognitive-behavioral clinical trials literature," Sleep Medicine Reviews, YSMRV 286, pp. 1-14, (2003).
Goodrich at al., "The Prediction of Pain Using Measures of Sleep Quality," Pain Digest, 8:23-25, (1998).

"Analysis of heart rate dynamics by methods derived from nonlinear mathematics: Clinical applicability and prognostic significance" http:/herkules.oulu.fi.isbn9514250133/html, 4 pgs., (2004).
Kerr et al., "Analysis of the sit-stand-sit movement cycle in normal subjects," Clinical Biomechanics, vol. 12, No. 4, pp. 236-245, (1997).
Aminian et al. "Physical Activity Monitoring Based on Accelerometry: Validation and Comparison with Video Observation," Medical & Biological Engineering & Computing, vol. 37, No. 2, pp. 304-308 (1999).
Medcare—A Global Leader in Sleep Diagnostics, Embletta Recording System, http://www.medcare.com/products/diagnostic/embletta/, 2 pgs. Jan. 31, 2005.
Medcare—A Global Leader in Sleep Diagnostics, Somnologica for Embletta, http://www.medcare.com/products/diagnostic/embletta/SomnoEmbletta/index.asp, 1 pg. Jan. 31, 2005.
MAP Medizin-Technologie GmbH, Poly-MESAM®, http://195.244.124.130/map/de/eng/map_med.nsf/smsall/70564A3FCBE4188AC1256EF4.., 4 pgs. Jan. 31, 2005.
Merlin, http://www.aha.ru/~pir/english/merlin/, 4 pgs. Jan. 31, 2005.
Sleep Solutions—PR Newswire: Sleep Solutions Introduces NovaSom™ QSG™ for PSG.., http://www.sleep-solutions.com/press_room/novasom.htm, 2 pgs. Jan. 31, 2005.
Itamar Medical Information, http://itamar-medical.com/content.asp?id-id=31, 2 pgs. Jan. 31, 2005.
Criticare System Inc.,-504DX Portable Pulse Oximeter, http://www.csiusa.com/504dx.html, 4 pgs. Jan. 31, 2005.
Snap® Laboratories, Product Fact Sheet, http://www.snaplab.com/mp_fact.htm, 2 pgs. Jan. 31, 2005.
Sleep Strip & Bite Strip, http://ww.quietsleep.com/snoringapnea/sleepstrip.htm, 8 pgs. Jan. 31, 2005.
"Bitestrip Flier," downloaded from Internet Archive of www.quietsleep.com dated Jan. 29, 2005 http://web.archive.org/web/2004112408003/www.quietsleep.com/pdf/Bitestrip+Flier.pdf.
"Bilateral Comparisons of the BiteStrip Bruxism Device and Masseter EMG Bruxism Events"downloaded from Internet Archive of www.quietsleep.com dated Jan. 29, 2005 http://web.archive.org/web/20041124075114/www.quietsleep.com/pdf/Bilateral+Comparisons.pdf.
"The BiteStrip: A Novel Screener for Sleep Bruxism," downloaded from Internet Archive of www.quietsleep.com dated Jan. 29, 2005 http://web.archive.org/web/20041124072922/www.quietsleep.com/pdf/BiteStrip-+Novel+Screener.pdf.
Office Action dated Jul. 20, 2006 for U.S. Appl. No. 10/825,955, filed Apr. 15, 2004, (10 pgs.).
Responsive Amendment dated Oct. 20, 2006 for U.S. Appl. No. 10/825,955, filed Apr. 15, 2004 (21 pgs.).
Office Action dated Jan. 17, 2007 for U.S. Appl. No. 10/825,955, filed Apr. 15, 2004, (10 pgs.).
Responsive Amendment dated Mar. 19, 2007 for U.S. Appl. No. 10/825,955, filed Apr. 15, 2004 (13 pgs.).
Office Action dated Jun. 27, 2007 for U.S. Appl. No. 10/825,955, filed Apr. 15, 2004, (13 pgs.).
Office Action dated Jul. 3, 2007 for U.S. Appl. No. 10/826,925, filed Apr. 15, 2004, (22 pgs.).
Responsive Amendment dated Aug. 4, 2008 for U.S. Appl. No. 11/081,155 (12 pgs.).
Responsive Amendment dated Aug. 7, 2008 for U.S. Appl. No. 11/081,857 (13 pgs.).
Response dated Aug. 22, 2008 for U.S. Appl. No. 10/826,925 (7 pgs.).
Responsive Amendment dated Aug. 29, 2008 for U.S. Appl. No. 11/081,811 (13 pgs.).
Request for Continued Examinatin and Amendment dated Jul. 28, 2010 for U.S. Appl. No. 11/081,811 (19 pgs.).
Office Action dated Apr. 28, 2010 for U.S. Appl. No. 11/081,811 (18 pgs.).
Responsive Amendment dated Aug. 5, 2010 for U.S. Appl. No. 12/248,622 (10 pgs.).
Office Action dated Dec. 21, 2009 for U.S. Appl. No. 11/691,405 (11 pgs.).
Office Action dated Feb. 2, 2010 for U.S. Appl. No. 12/351,414 (11 pgs.).

Responsive Amendment dated Mar. 22, 2010 for U.S. Appl. No. 11/691,405 (18 pgs.).
Office Action dated Mar. 12, 2010 for U.S. Appl. No. 11/691,413 (7 pgs.).
Office Action dated May 19, 2010 for U.S. Appl. No. 11/691,405 (12 pgs.).
Office Action dated May 20, 2010 for U.S. Appl. No. 12/248,622 (6 pgs.).
Responsive Amendment dated Jun. 9, 2010 for U.S. Appl. No. 11/691,413 (16 pgs.).
Response dated Jun. 2, 2010 for U.S. Appl. No. 12/351,414 (8 pgs.).
Office Action dated Oct. 14, 2009 for U.S. Appl. No. 11/081,857 (14 pgs.).
Reponse dated Dec. 14, 2009 for U.S. Appl. No. 11/081,857 (8 pgs.).
Advisory Action dated Jan. 12, 2010 for U.S. Appl. No. 11/081,857 (3 pgs.).
Office Action dated May 19, 2010 for U.S. Appl. No. 11/691,405 (12 pgs.).
Request for Continued Examination and Amendment dated Aug. 19, 2010 for U.S. Appl. No. 11/691,405 (17 pgs.).

CONTROLLING THERAPY BASED ON SLEEP QUALITY

This application is a continuation-in-part of U.S. application Ser. No. 11/081,155, filed Mar. 16, 2005, which is a continuation-in-part of U.S. application Ser. No. 10/825,953, filed Apr. 15, 2004, which claims the benefit of U.S. provisional application No. 60/553,777, filed Mar. 16, 2004. This application also claims the benefit of U.S. Provisional Application No. 60/785,819, filed Mar. 24, 2006. The entire content of each of these applications is incorporated herein by reference.

TECHNICAL FIELD

The invention relates to medical devices and, more particularly, to medical devices that deliver a therapy.

BACKGROUND

In some cases, an ailment that a patient has may affect the quality of the patient's sleep. For example, chronic pain may cause a patient to have difficulty falling asleep, and may disturb the patient's sleep, e.g., cause the patient to wake. Further, chronic pain may cause the patient to have difficulty achieving deeper sleep states, such as the nonrapid eye movement (NREM) sleep state.

Other ailments that may negatively affect patient sleep quality include movement disorders, such as tremor, Parkinson's disease, multiple sclerosis, epilepsy, or spasticity. The uncontrolled movements associated with such movement disorders may cause a patient to have difficulty falling asleep, disturb the patient's sleep, or cause the patient to have difficulty achieving deeper sleep states. Psychological disorders, such as depression, mania, bipolar disorder, or obsessive-compulsive disorder, as well as sleep apnea, congestive heart failure, gastrointestinal disorders and incontinence may also similar affect the ability of a patient to sleep, or at least experience quality sleep. In the case of depression, a patient may "sleep" for long periods of the day, but the sleep is not restful, e.g., includes excessive disturbances and does not include deeper, more restful sleep states. In some cases, these ailments are treated via an implantable medical device (IMD), such as an implantable stimulator or drug delivery device. Movement disorders and psychological disorders are examples of neurological disorders.

Further, in some cases, poor sleep quality may increase the symptoms experienced by a patient due to an ailment. For example, poor sleep quality has been linked to increased pain symptoms in chronic pain patients, and may also result in increased movement disorder symptoms in movement disorder patients. Further, poor sleep quality may exacerbate many psychological disorders, such as depression. The link between poor sleep quality and increased symptoms is not limited to ailments that negatively impact sleep quality, such as those listed above. Nonetheless, the condition of a patient with such an ailment may progressively worsen when symptoms disturb sleep quality, which in turn increases the frequency and/or intensity of symptoms.

SUMMARY

In general, the invention is directed to techniques for controlling delivery of a therapy to a patient by a medical device, such as an implantable medical device (IMD), based on the quality of sleep experienced by a patient. In particular, a medical device according to the invention determines values for one or more metrics that indicate the quality of a patient's sleep, and controls delivery of a therapy based on the sleep quality metric values. A medical device according to the invention may be able to adjust the therapy to address symptoms or ailments causing disturbed sleep or symptoms or ailments that are worsened by disturbed sleep, such as chronic pain, movement disorders, or psychological disorders.

The medical device monitors one or more physiological parameters of the patient in order to determine values for the one or more sleep quality metrics. Example physiological parameters that the medical device may monitor include activity level, posture, heart rate, electrocardiogram (ECG) morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, melatonin level within one or more bodily fluids, brain electrical activity, such as electroencephalogram (EEG) morphology, eye motion, and galvanic skin response. In some embodiments, the medical device additionally or alternatively monitors the variability of one or more of these parameters. In order to monitor one or more of these parameters, the medical device may include, be coupled to, or be in wireless communication with one or more sensors, each of which outputs a signal as a function of one or more of these physiological parameters.

Sleep efficiency and sleep latency are example sleep quality metrics for which a medical device according to the invention may determine values. Sleep efficiency may be measured as the percentage of time while the patient is attempting to sleep that the patient is actually asleep. Sleep latency may be measured as the amount of time between a first time when begins attempting to sleep and a second time when the patient falls asleep.

The time when the patient begins attempting to fall asleep may be determined in a variety of ways. For example, the medical device may receive an indication from the patient that the patient is trying to fall asleep, e.g., via a patient programming device in embodiments in which the medical device is an implantable medical device. In other embodiments, the medical device may monitor the activity level of the patient, determining whether the patient has remained inactive for a threshold period of time, and identify the time at which the patient became inactive as the time at which the patient begin attempting to fall asleep. In still other embodiments, the medical device may monitor patient posture, and identify the time when the patient is recumbent, e.g., lying down, as the time when the patient is attempting to fall asleep. In these embodiments in which the medical device determines when the patient is recumbent, the medical device may also monitor patient activity, and the medical may confirm that the patient is attempting to sleep based on the patient's activity level.

As another example, the medical device may determine the time at which the patient begins attempting to fall asleep based on the level of melatonin within one or more bodily fluids, such as the patient's blood, cerebrospinal fluid (CSF), or interstitial fluid. The medical device may also determine a melatonin level based on metabolites of melatonin located in the saliva or urine of the patient. Melatonin is a hormone secreted by the pineal gland into the bloodstream and the CSF as a function of exposure of the optic nerve to light, which synchronizes the patient's circadian rhythm. In particular, increased levels of melatonin during evening hours may cause physiological changes in the patient, which, in turn, may cause the patient to attempt to fall asleep. The medical device may, for example, detect an increase in the level of melatonin, and estimate the time that the patient will attempt to fall asleep based on the detection.

The medical device may determine the time at which the patient has fallen asleep based on the activity level of the patient and/or one or more of the other physiological parameters that may be monitored by the medical device as indicated above. For example, a discernable change, e.g., a decrease, in one or more physiological parameters, or the variability of one or more physiological parameters, may indicate that the patient has fallen asleep. In some embodiments, the medical device may determine a sleep probability metric value based on a value of a physiological parameter. In such embodiments, the medical device may compare the sleep probability metric value to a threshold to identify when the patient has fallen asleep. In some embodiments, the medical device may determine a plurality of sleep probability metric values based on a value of each of a plurality of physiological parameters, average or otherwise combine the plurality of sleep probability metric values to provide an overall sleep probability metric value, and compare the overall sleep probability metric value to a threshold to identify the time that the patient falls asleep.

Other sleep quality metrics that the medical device may determine include total time sleeping per day, the amount or percentage of time sleeping during nighttime or daytime hours per day, and the number of apnea and/or arousal events per night. In some embodiments, the medical device may be able to determine which sleep state the patient is in, e.g., rapid eye movement (REM), or one of the nonrapid eye movement (NREM) states (S1, S2, S3, S4), and the amount of time per day spent in these various sleep states may be determined as a sleep quality metric. Because they provide the most "refreshing" type of sleep, the amount of time spent in one or both of the S3 and S4 sleep states, in particular, may be determined as a sleep quality metric. In some embodiments, the medical device may determine average or median values of one or more sleep quality metrics over greater periods of time, e.g., a week or a month, as the value of the sleep quality metric. Further, in embodiments in which the medical device collects values for a plurality of the sleep quality metrics identified above, the medical device may determine a value for an overall sleep quality metric based on the collected values for the plurality of sleep quality metrics.

The medical device controls delivery of therapy based on determined sleep quality metric values. For example, the medical device may compare a current, a mean, a median, or an overall sleep quality metric value with one or more threshold values, and adjust the therapy based on the comparison. In some embodiments, the medical device adjusts the intensity of therapy based on the comparison, e.g., increases the therapy intensity when the comparison indicates that the patient's sleep quality is poor. In embodiments in which the medical device is a neurostimulator, for example, the pulse amplitude, pulse width, pulse rate, or duty cycle of delivered neurostimulation can be adjusted. As another example, in embodiments in which the medical device is a pump, the dosage or infusion rate of a therapeutic agent delivered by the pump can be adjusted.

In some embodiments, the medical device delivers therapy according to a current set of therapy parameters. The current therapy parameter set may be a selected one of a plurality of therapy parameter sets specified by a clinician. The currently selected therapy one of these preprogrammed parameter sets may be selected by a processor of the medical device, e.g., according to a therapy schedule, or by the patient using a patient programmer. A current therapy parameter set may also be the result of the patient modifying one or more parameters of a preprogrammed parameter set. In either case, the medical device identifies the current therapy parameter set when a value of one or more sleep quality metrics is collected, and may associate that value with the current therapy parameter set.

For example, for each of a plurality of therapy parameter sets, the medical device may store a representative value of each of one or more sleep quality metrics in a memory with an indication of the therapy parameter set with which the representative value is associated. A representative value of sleep quality metric for a therapy parameter set may be the mean or median of collected sleep quality metric values that have been associated with that therapy parameter set. In some embodiments, the medical device controls delivery of therapy according to sleep quality metric values by automatically selecting one of the plurality therapy parameter sets for use in delivering therapy based on a comparison of their representative sleep quality metric values, e.g., automatically selects the therapy parameter set whose representative values indicate the highest sleep quality.

In one embodiment, the invention is directed to a method comprising monitoring at least one physiological parameter of a patient via a medical device that delivers at least one of a movement disorder therapy, psychological disorder therapy, or deep brain stimulation to a patient, determining a value of a metric that is indicative of sleep quality is determined based on the at least one physiological parameter, and delivering the at least one of the movement disorder therapy, psychological disorder therapy, or deep brain stimulation to the patient by the medical device is controlled based on the sleep quality metric value.

In another embodiment, the invention is directed to a medical device comprising a therapy module to deliver at least one of a movement disorder therapy, psychological disorder therapy, or deep brain stimulation to a patient and a processor. The processor monitors at least one physiological parameter of a patient based on at least one signal received from at least one sensor, determines a value of a metric that is indicative of sleep quality based on the at least one physiological parameter, and controls delivery of the at least one of the movement disorder therapy, psychological disorder therapy, or deep brain stimulation to the patient by the therapy module based on the sleep quality metric value.

In another embodiment, the invention is directed to a computer-readable medium containing instructions. The instructions cause a programmable processor to monitor at least one physiological parameter of a patient via a medical device delivers at least one of a movement disorder therapy, psychological disorder therapy, or deep brain stimulation to the patient, determine a value of a metric that is indicative of sleep quality based on the at least one physiological parameter, and control delivery of the at least one of the movement disorder therapy, psychological disorder therapy, or deep brain stimulation to the patient by the medical device based on the sleep quality metric value.

The invention is capable of providing one or more advantages. For example, a medical device according to the invention may be able to adjust the therapy to address symptoms or ailments causing disturbed sleep, or symptoms that are worsened by disturbed sleep. Adjusting therapy based on sleep quality information may significantly improve the patient's sleep quality and condition. The ability of a medical device to adjust therapy based on sleep quality may be particularly advantageous in embodiments in which the medical device delivers the therapy to treat chronic pain, movement disorders, or psychological disorders, which may both disturb sleep and be worsened by disturbed sleep. Moreover, the ability of the medical device to both automatically identify a need for therapy adjustment and automatically adjust the therapy may reduce the need for the patient to make time consuming and expensive clinic visits when the patient's sleep is disturbed or symptoms have worsened.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
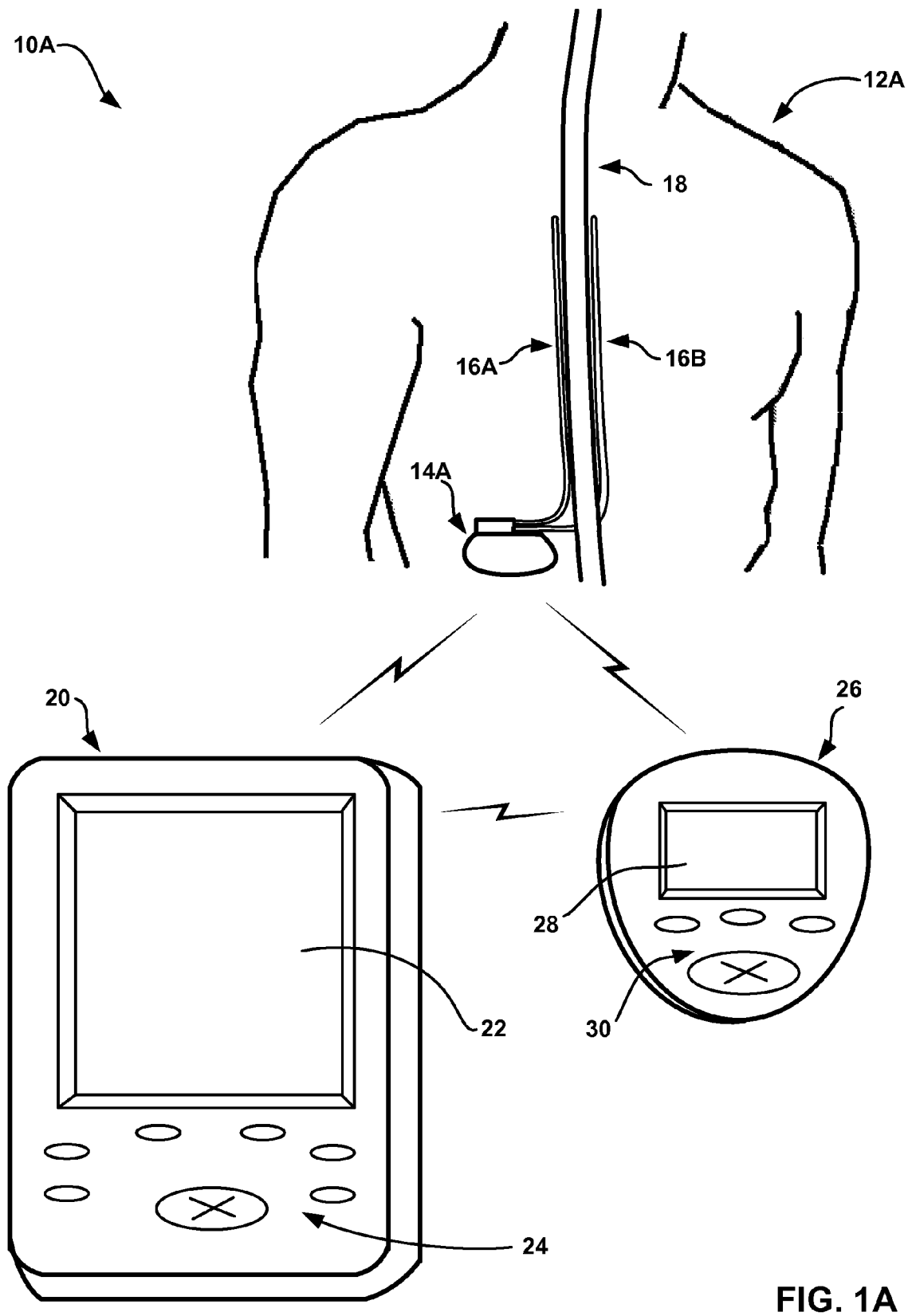
FIGS. 1A and 1B are conceptual diagrams illustrating example systems that include an implantable medical device that controls delivery of therapy based on sleep quality information according to the invention.
Figure 1B:
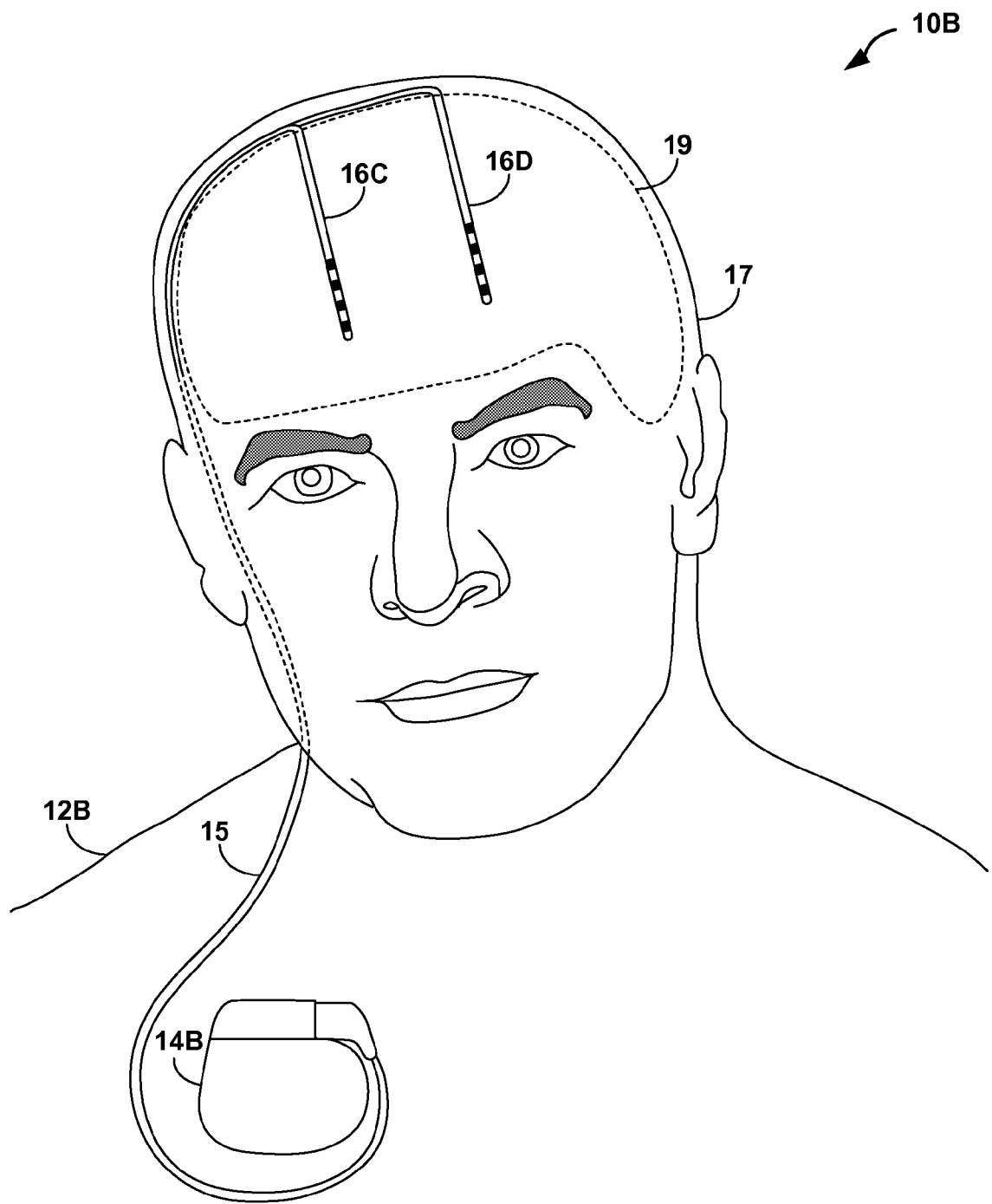

FIGS. 1A and 1B are conceptual diagrams illustrating example systems 10A and 10B (collectively "systems 10") that respectively include an implantable medical device (IMD) 14A or 14B (collectively "IMDs 14") that controls delivery of a therapy to a respective one of patients 12A and 12B (collectively "patients 12") based on sleep quality information. In particular, as will be described in greater detail below, IMDs 14 may be provided to determine values for one or more metrics that indicate the quality of sleep experienced by patients 12, and control delivery of the therapy based on the sleep quality metric values. IMDs 14 may be able to adjust the therapy to address one or more symptoms or ailments causing disturbed sleep, or symptoms or ailments that are worsened by disturbed sleep. In exemplary embodiments, IMDs 14 deliver a therapy to treat chronic pain or any neurological disorders such as movement disorders or psychological disorders, which may both negatively impact the quality of sleep experienced by patients 12, and be worsened by inadequate sleep quality.

In the illustrated example systems 10, IMDs 14 take the form of an implantable neurostimulators that deliver neurostimulation therapy in the form of electrical pulses to patients 12. IMDs 14 deliver neurostimulation therapy to patients 12A and 12B via leads 16A and 16B, and leads 16C and 16D (collectively "leads 16"), respectfully. Leads 16 may, as shown in FIG. 1A, be implanted proximate to the spinal cord 18 of patient 12A, and IMD 14A may deliver spinal cord stimulation (SCS) therapy to patient 12A in order to, for example, reduce pain experienced by patient 12A. However, the invention is not limited to the configuration of leads 16 shown in FIG. 1A, or to the delivery of SCS therapy. For example, in another embodiment, illustrated in FIG. 1B, leads 16C and 16D may extend to brain 19 of patient 12B, e.g., through cranium 17 of patient. IMD 14B may deliver deep brain stimulation (DBS) or cortical stimulation therapy to patient 12 to treat any of a variety of non-respiratory neurological disorders, such as movement disorders or psychological disorders. In general, non-respiratory neurological disorders exclude respiratory disorders, such as sleep apnea. Example therapies may treat tremor, Parkinson's disease, spasticity, epilepsy, depression or obsessive-compulsive disorder. As illustrated in FIG. 1B, leads 16C and 16D may be coupled to IMD 14B via one or more lead extensions 15.

As further examples, one or more leads 16 may be implanted proximate to the pelvic nerves (not shown) or stomach (not shown), and an IMD 14 may deliver neurostimulation therapy to treat incontinence or gastroparesis. Additionally, leads 16 may be implanted on or within the heart to treat any of a variety of cardiac disorders, such as congestive heart failure or arrhythmia, or may be implanted proximate to any peripheral nerves to treat any of a variety of disorders, such as peripheral neuropathy or other types of chronic pain.

The illustrated numbers and locations of leads 16 are merely examples. Embodiments of the invention may include any number of lead implanted at any of a variety of locations within a patient. Furthermore, the illustrated number and location of IMDs 14 are merely examples. IMDs 14 may be located anywhere within patient according to various embodiments of the invention. For example, in some embodiments, an IMD 14 may be implanted on or within cranium 17 for delivery of therapy to brain 19, or other structure of the head of the patient 12.

Moreover, the invention is not limited to implementation via an implantable neurostimulator, or even implementation via an IMD. For example, in some embodiments of the invention, an implantable or external stimulator or drug delivery device may control delivery of a therapy based on sleep quality information. In other words, any implantable or external medical device that delivers a therapy may control delivery of the therapy based on collected sleep quality information according to the invention.

In the example of FIGS. 1A and 1B, IMDs 14 deliver therapy according to a set of therapy parameters, i.e., a set of values for a number of parameters that define the therapy delivered according to that therapy parameter set. In embodiments where an IMD 14 delivers neurostimulation therapy in the form of electrical pulses, the parameters for each parameter set may include voltage or current pulse amplitudes, pulse widths, pulse rates, and the like. Further, each of leads 16 includes electrodes (not shown in FIGS. 1A and 1B), and a therapy parameter set may include information identifying which electrodes have been selected for delivery of pulses, and the polarities of the selected electrodes. In embodiments in which IMDs 14 deliver other types of therapies, therapy parameter sets may include other therapy parameters such as drug concentration and drug flow rate in the case of drug delivery therapy. Therapy parameter sets used by an IMD 14 may include a number of parameter sets programmed by a clinician (not shown), and parameter sets representing adjustments made by a patient 12 to these preprogrammed sets.

In other non-neurostimulator embodiments of the invention, the IMD may still deliver therapy according to a therapy parameter set. For example, implantable pump IMD embodiments may deliver a therapeutic agent to a patient according to a therapy parameter set that includes, for example, a dosage, an infusion rate, and/or a duty cycle.

Each of systems 10 may also include a clinician programmer 20 (illustrated as part of system 10A in FIG. 1A). A clinician (not shown) may use clinician programmer 20 to program therapy for patient 12A, e.g., specify a number of therapy parameter sets and provide the parameter sets to IMD 14A. The clinician may also use clinician programmer 20 to retrieve information collected by IMD 14A. The clinician may use clinician programmer 20 to communicate with IMD 14A both during initial programming of IMD 14A, and for collection of information and further programming during follow-up visits.

Clinician programmer 20 may, as shown in FIG. 1A, be a handheld computing device. Clinician programmer 20 includes a display 22, such as a LCD or LED display, to display information to a user. Clinician programmer 20 may also include a keypad 24, which may be used by a user to interact with clinician programmer 20. In some embodiments, display 22 may be a touch screen display, and a user may interact with clinician programmer 20 via display 22. A user may also interact with clinician programmer 20 using peripheral pointing devices, such as a stylus, mouse, or the like. Keypad 24 may take the form of an alphanumeric keypad or a reduced set of keys associated with particular functions.

Systems 10 may also includes a patient programmer 26 (illustrated as part of system 10A in FIG. 1A), which also may, as shown in FIG. 1A, be a handheld computing device. Patient 12A may use patient programmer 26 to control the delivery of therapy by IMD 14A. For example, using patient programmer 26, patient 12A may select a current therapy parameter set from among the therapy parameter sets preprogrammed by the clinician, or may adjust one or more parameters of a preprogrammed therapy parameter set to arrive at the current therapy parameter set.

Patient programmer 26 may also include a display 28 and a keypad 30 to allow patient 12A to interact with patient programmer 26. In some embodiments, display 28 may be a touch screen display, and patient 12A may interact with patient programmer 26 via display 28. Patient 12A may also interact with patient programmer 26 using peripheral pointing devices, such as a stylus, mouse, or the like.

However, clinician and patient programmers 20, 26 are not limited to the hand-held computer embodiments illustrated in FIG. 1A. Programmers 20, 26 according to the invention may be any sort of computing device. For example, a programmer 20, 26 according to the invention may a tablet-based computing device, a desktop computing device, or a workstation.

IMDs 14, clinician programmers 20 and patient programmers 26 may, as shown in FIG. 1A, communicate via wireless communication. Clinician programmer 20 and patient programmer 26 may, for example, communicate via wireless communication with IMD 14A using radio frequency (RF) telemetry techniques known in the art. Clinician programmer 20 and patient programmer 26 may communicate with each other using any of a variety of local wireless communication techniques, such as RF communication according to the 802.11 or Bluetooth specification sets, infrared communication according to the IRDA specification set, or other standard or proprietary telemetry protocols.

Clinician programmer 20 and patient programmer 26 need not communicate wirelessly, however. For example, programmers 20 and 26 may communicate via a wired connection, such as via a serial communication cable, or via exchange of removable media, such as magnetic or optical disks, or memory cards or sticks. Further, clinician programmer 20 may communicate with one or both of IMD 14 and patient programmer 26 via remote telemetry techniques known in the art, communicating via a local area network (LAN), wide area network (WAN), public switched telephone network (PSTN), or cellular telephone network, for example.

As mentioned above, IMDs 14 controls delivery of a therapy, e.g., neurostimulation, to patients 12 based on the quality sleep experienced by the patients. In particular, as will be described in greater detail below, IMDs 14 determine values for one or more metrics that indicate the quality of sleep experienced by patients 12. IMDs 14 controls delivery of the therapy to patients 12, e.g., adjusts the therapy, based on the sleep quality metric values.

IMDs 14 monitor one or more physiological parameters of the patient in order to determine values for the one or more sleep quality metrics. Example physiological parameters that IMD 14 may monitor include activity level, posture, heart rate, ECG morphology, respiration rate, respiratory volume, blood pressure, blood oxygen saturation, partial pressure of oxygen within blood, partial pressure of oxygen within cerebrospinal fluid (CSF), muscular activity and tone, core temperature, subcutaneous temperature, arterial blood flow, the level of melatonin within one or more bodily fluids, brain electrical activity, electroencephalogram (EEG) morphology, and eye motion. Some external medical device embodiments of the invention may additionally or alternatively monitor galvanic skin response. Further, in some embodiments IMDs 14 additionally or alternatively monitors the variability of one or more of these parameters. In order to monitor one or more of these parameters, IMDs 14 may include, be coupled to, or be in wireless communication with one or more sensors (not shown in FIGS. 1A and 1B), each of which outputs a signal as a function of one or more of these physiological parameters.

For example, an IMD 14 may determine sleep efficiency and/or sleep latency values. Sleep efficiency and sleep latency are example sleep quality metrics. IMDs 14 may measure sleep efficiency as the percentage of time while a patient 12 is attempting to sleep that the patient 12 is actually asleep. An IMD 14 may measure sleep latency as the amount of time between a first time when a patient 12 begins attempting to sleep and a second time when a patient 12 falls asleep, e.g., as an indication of how long it takes the patient 12 to fall asleep.

An IMD 14 may identify the time at which patient begins attempting to fall asleep in a variety of ways. For example, an IMD 14 may receive an indication from the patient that the patient is trying to fall asleep via patient programmer 26. In other embodiments, an IMD 14 may monitor the activity level of a patient 12, and identify the time when the patient 12 is attempting to fall asleep by determining whether the patient 12 has remained inactive for a threshold period of time, and identifying the time at which the patient 12 became inactive. In still other embodiments, an IMD 14 may monitor the posture of a patient 12, and may identify the time when the patient 12 becomes recumbent, e.g., lies down, as the time when the patient 12 is attempting to fall asleep. In these embodiments, an IMD 14 may also monitor the activity level of a patient 12, and confirm that the patient 12 is attempting to sleep based on the activity level.

As another example, an IMD 14 may determine the time at which a patient 12 is attempting to fall asleep based on the level of melatonin within one or more bodily fluids of the patient 12, such as the patient's blood, cerebrospinal fluid (CSF), or interstitial fluid. IMD 14 may also determine a melatonin level based on metabolites of melatonin located in the saliva or urine of the patient. Melatonin is a hormone secreted by the pineal gland into the bloodstream and the CSF as a function of exposure of the optic nerve to light, which synchronizes the patient's circadian rhythm. In particular, increased levels of melatonin during evening hours may cause physiological changes in a patient 12, which, in turn, may cause the patient 12 to attempt to fall asleep.

An IMD 14 may, for example, detect an increase in the level of melatonin in a bodily fluid, and estimate the time that patient 12 will attempt to fall asleep based on the detection. For example, an IMD 14 may compare the melatonin level or rate of change in the melatonin level to a threshold level, and identify the time that threshold value is exceeded. An IMD 14 may identify the time that a patient 12 is attempting to fall asleep as the time that the threshold is exceeded, or some amount of time after the threshold is exceeded.

An IMD 14 may identify the time at which a patient 12 has fallen asleep based on the activity level of the patient and/or one or more of the other physiological parameters that may be monitored by the IMD 14 as indicated above. For example, an IMD 14 may identify a discernable change, e.g., a decrease, in one or more physiological parameters, or the variability of one or more physiological parameters, which may indicate that a patient 12 has fallen asleep. In some embodiments, an IMD 14 determines a sleep probability metric value based on a value of a physiological parameter monitored by the medical device. In such embodiments, the sleep probability metric value may be compared to a threshold to identify when the patient has fallen asleep. In some embodiments, a sleep probability metric value is determined based on a value of each of a plurality of physiological parameters, the sleep probability values are averaged or otherwise combined to provide an overall sleep probability metric value, and the overall sleep probability metric value is compared to a threshold to identify the time that the patient falls asleep.

Other sleep quality metrics include total time sleeping per day, and the amount or percentage of time sleeping during nighttime or daytime hours per day. In some embodiments, an IMD 14 may be able to detect arousal events and apneas occurring during sleep based on one or more monitored physiological parameters, and the number of apnea and/or arousal events per night may be determined as a sleep quality metric. Further, in some embodiments an IMD 14 may be able to determine which sleep state a patient 12 is in based on one or more monitored physiological parameters, e.g., rapid eye movement (REM), S1, S2, S3, or S4, and the amount of time per day spent in these various sleep states may be a sleep quality metric.

The S3 and S4 sleep states may be of particular importance to the quality of sleep experienced by a patient 12. Interruption from reaching these states, or inadequate time per night spent in these states, may cause a patient 12 to not feel rested. For this reason, the S3 and S4 sleep states are believed to provide the "refreshing" part of sleep.

In some cases, interruption from reaching the S3 and S4 sleep states, or inadequate time per night spent in these states has been demonstrated to cause normal subjects to exhibit some symptoms of fibromyalgia. Also, subjects with fibromyalgia usually do not reach these sleep states. For these reasons, in some embodiments, an IMD 14 may determine an amount or percentage of time spent in one or both of the S3 and S4 sleep states as a sleep quality metric.

In some embodiments, an IMD 14 may determine average or median values of one or more sleep quality metrics over greater periods of time, e.g., a week or a month, as the value of the sleep quality metric. Further, in embodiments in which an IMD 14 collects values for a plurality of the sleep quality metrics identified above, the IMD 14 may determine a value for an overall sleep quality metric based on the collected values for the plurality of sleep quality metrics. An IMD 14 may determine the value of an overall sleep quality metric by applying a function or look-up table to a plurality of sleep quality metric values, which may also include the application of weighting factors to one or more of the individual sleep quality metric values.

In some embodiments, an IMD 14 compares a current, a mean, a median, or an overall sleep quality metric value with one or more threshold values, and adjusts the therapy delivered by the IMD 14 based on the comparison. In such embodiments, an IMD 14 may adjust the intensity of the therapy based on the comparison. For example, an IMD 14 may increase the intensity of the therapy when the comparison indicates that the sleep quality experienced by a patient 12 is poor in order to address the symptoms which are disturbing the patient's sleep, and/or to address the increase in symptoms which may result from the disturbed sleep.

For example, in embodiments such that illustrated by FIGS. 1A and 1B in which an IMD 14 is a neurostimulator, the IMD 14 may increase the pulse amplitude, pulse width, pulse rate, or duty cycle, e.g., duration, of delivered neurostimulation. As another example, in embodiments in which an IMD is an implantable pump, the IMD may increase the dosage, infusion rate, or duty cycle of a therapeutic agent delivered by the pump. An IMD 14 may adjust such parameters within ranges specified by a clinician or a manufacturer of the IMD 14.

In some embodiments, an IMD 14 may iteratively and incrementally increase the intensity so long as the comparison indicates poor sleep quality. In other embodiments, an IMD 14 may substantially increase the intensity of the therapy when the comparison indicates poor sleep quality in order to more quickly identify an efficacious operating point. In some embodiments, an IMD 14 may gradually decrease the intensity of the therapy so long as the comparison indicates that the sleep quality experienced by a patient 12 is adequate to, for example, conserve the energy stored by a battery of an IMD 14. In other embodiments, the amount by which an IMD 14 increases or decreases the intensity of therapy may be proportional to the difference or ratio between the current sleep quality metric value and the threshold value.

In some embodiments, an IMD 14 may identify the current therapy parameter set when a value of one or more sleep quality metrics is collected, and may associate that value with the current therapy parameter set. For example, for each of a plurality of therapy parameter sets, an IMD 14 may store a representative value of each of one or more sleep quality metrics in a memory with an indication of the therapy parameter with which that representative value is associated. A representative value of sleep quality metric for a therapy parameter set may be the mean or median of collected sleep quality metric values that have been associated with that therapy parameter set. In some embodiments, an IMD 14 controls delivery of therapy according to sleep quality metric values by automatically selecting one of the plurality of therapy parameter sets for use in delivering therapy based on a comparison of their representative sleep quality metric values, e.g., automatically select the therapy parameter set whose representative sleep quality metric values indicate the highest sleep quality.

Figure 2A:
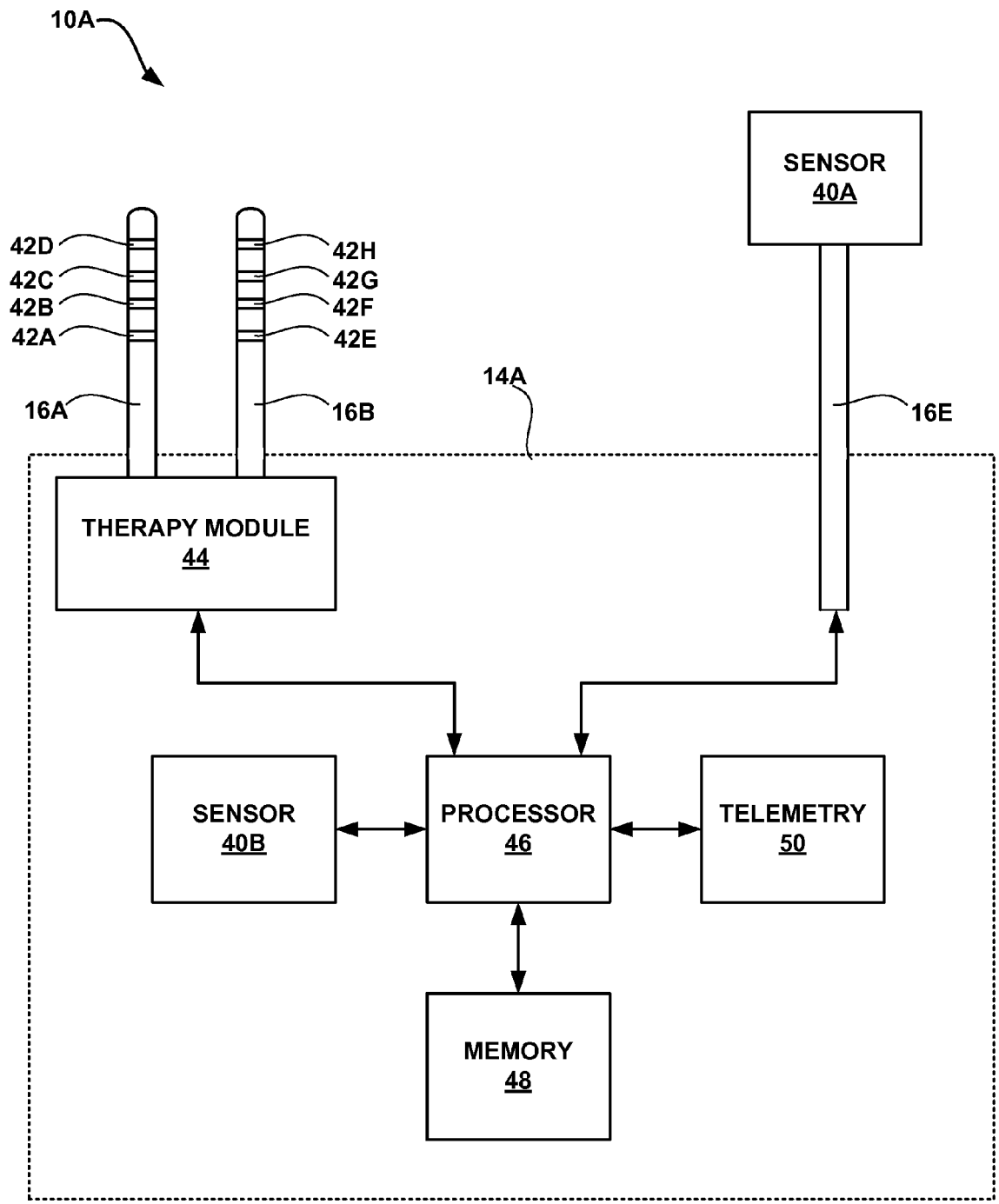
FIGS. 2A and 2B are block diagrams further illustrating the example systems and implantable medical devices of FIGS. 1A and 1B.
Figure 2B:
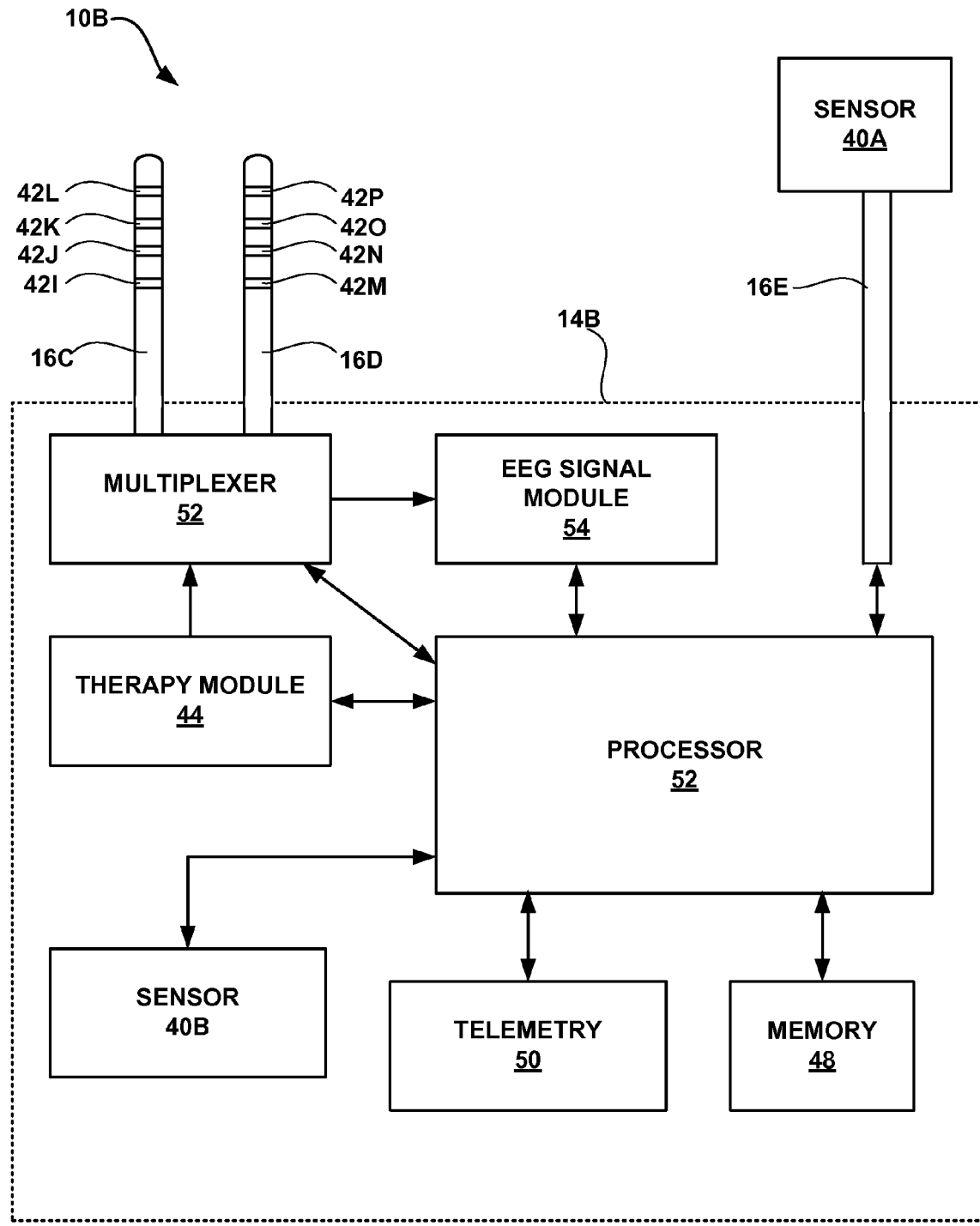

FIGS. 2A and 2B are block diagrams further illustrating systems 10A and 10B. In particular, FIG. 2A illustrates an example configuration of IMD 14A and leads 16A and 16B. FIG. 2B illustrates an example configuration of IMD 14B and leads 16C and 16D. FIGS. 2A and 2B also illustrate sensors 40A and 40B (collectively "sensors 40") that output signals as a function of one or more physiological parameters of patients 12.

IMD 14A may deliver neurostimulation therapy via electrodes 42A-D of lead 16A and electrodes 42E-H of lead 16B, while IMD 14B delivers neurostimulation via electrodes 42I-L of lead 16C and electrodes 42 M-P of lead 16D (collectively "electrodes 42"). Electrodes 42 may be ring electrodes. The configuration, type and number of electrodes 42 illustrated in FIGS. 2A and 2B are merely exemplary. For example, leads 16 may each include eight electrodes 42, and the electrodes 42 need not be arranged linearly on each of leads 16.

In each of systems 10A and 10B, electrodes 42 are electrically coupled to a therapy delivery module 44 via leads 16. Therapy delivery module 44 may, for example, include an output pulse generator coupled to a power source such as a battery. Therapy delivery module 44 may deliver electrical pulses to a patient 12 via at least some of electrodes 42 under the control of a processor 46, which controls therapy delivery module 44 to deliver neurostimulation therapy according to one or more neurostimulation therapy parameter sets selected from available parameter sets stored in a memory 48. However, the invention is not limited to implantable neurostimulator embodiments or even to IMDs that deliver electrical stimulation. For example, in some embodiments a therapy delivery module of an IMD may include a pump, circuitry to control the pump, and a reservoir to store a therapeutic agent for delivery via the pump, and a processor of the IMD may control delivery of a therapeutic agent by the pump according to an infusion parameter set selected from among a plurality of infusion parameter sets stored in a memory.

An IMD 14 may also include a telemetry circuit 50 that enables processor 46 to communicate with programmers 20, 26. Via telemetry circuit 50, processor 46 may receive therapy parameter sets specified by a clinician from clinician programmer 20 for storage in memory 48. Processor 46 may also receive therapy parameter set selections and therapy adjustments made by a patient 12 using patient programmer 26 via telemetry circuit 50. In some embodiments, processor 46 may provide diagnostic information recorded by processor 46 and stored in memory 48 to one of programmers 20, 26 via telemetry circuit 50.

Processor 46 may include a microprocessor, a controller, a digital signal processor (DSP), an application specific integrated circuit (ASIC), a field-programmable gate array (FPGA), discrete logic circuitry, or the like. Memory 48 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, and the like. In some embodiments, memory 48 stores program instructions that, when executed by processor 46, cause an IMD 14 and processor 46 to perform the functions attributed to them herein.

Each of sensors 40 outputs a signal as a function of one or more physiological parameters of a patient 12. An IMD 14 may include circuitry (not shown) that conditions the signals output by sensors 40 such that they may be analyzed by processor 46. For example, an IMD 14 may include one or more analog to digital converters to convert analog signals output by sensors 40 into digital signals usable by processor 46, as well as suitable filter and amplifier circuitry. Although shown as including two sensors 40, systems 10 may include any number of sensors.

Further, as illustrated in FIGS. 2A and 2B, sensors 40 may be included as part of an IMD 14, or coupled to the IMD 14 via leads 16. Sensors 40 may be coupled to an IMD 14 via therapy leads 16A-16D, or via other leads 16, such as lead 16E depicted in FIGS. 2A and 2B. In some embodiments, a sensor located outside of an IMD 14 may be in wireless communication with processor 46. Wireless communication between sensors 40 and an IMD 14 may, as examples, include RF communication or communication via electrical signals conducted through the tissue and/or fluid of a patient 12.

As discussed above, exemplary physiological parameters of a patient 12 that may be monitored by an IMD 14 to determine values of one or more sleep quality metrics include activity level, posture, heart rate, ECG morphology, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, the level of melatonin within a bodily fluid of a patient 12, brain electrical activity, EEG morphology, and eye motion. Further, as discussed above, external medical device embodiments of the invention may additionally or alternatively monitor galvanic skin response. Sensors 40 may be of any type known in the art capable of outputting a signal as a function of one or more of these parameters.

In some embodiments, in order to determine one or more sleep quality metric values, processor 46 determines when a patient 12 is attempting to fall asleep. For example, processor 46 may identify the time that patient begins attempting to fall asleep based on an indication received from a patient 12, e.g., via clinician programmer 20 and a telemetry circuit 50. In other embodiments, processor 46 identifies the time that a patient 12 begins attempting to fall asleep based on the activity level of the patient 12.

In such embodiments, an IMD 14 may include one or more sensors 40 that generate a signal as a function of patient activity. For example, sensors 40 may include one or more accelerometers, gyros, mercury switches, or bonded piezoelectric crystals that generates a signal as a function of patient activity, e.g., body motion, footfalls or other impact events, and the like. Additionally or alternatively, sensors 40 may include one or more electrodes that generate an electromyogram (EMG) signal as a function of muscle electrical activity, which may indicate the activity level of a patient. The electrodes may be, for example, located in the legs, abdomen, chest, back or buttocks of a patient 12 to detect muscle activity associated with walking, running, or the like. The electrodes may be coupled to an IMD 14 wirelessly or by leads 16 or, if the IMD 14 is implanted in these locations, integrated with a housing of the IMD 14.

However, bonded piezoelectric crystals located in these areas generate signals as a function of muscle contraction in addition to body motion, footfalls or other impact events. Consequently, use of bonded piezoelectric crystals to detect activity of a patient 12 may be preferred in some embodiments in which it is desired to detect muscle activity in addition to body motion, footfalls, or other impact events. Bonded piezoelectric crystals may be coupled to an IMD 14 wirelessly or via leads 16, or piezoelectric crystals may be bonded to the housing of the IMD 14 when the IMD is implanted in these areas, e.g., in the back, chest, buttocks or abdomen of a patient 12.

Processor 46 may identify a time when the activity level of a patient 12 falls below a threshold activity level value stored in memory 48, and may determine whether the activity level remains substantially below the threshold activity level value for a threshold amount of time stored in memory 48. In other words, a patient 12 remaining inactive for a sufficient period of time may indicate that the patient 12 is attempting to fall asleep. If processor 46 determines that the threshold amount of time is exceeded, processor 46 may identify the time at which the activity level fell below the threshold activity level value as the time that a patient 12 began attempting to fall asleep.

In some embodiments, processor 46 determines whether a patient 12 is attempting to fall asleep based on whether the patient 12 is or is not recumbent, e.g., lying down. In such embodiments, sensors 40 may include a plurality of accelerometers, gyros, or magnetometers oriented orthogonally that generate signals which indicate the posture of a patient 12. In addition to being oriented orthogonally with respect to each other, each of sensors 40 used to detect the posture of a patient 12 may be generally aligned with an axis of the body of the patient 12. In exemplary embodiments, an IMD 14 includes three orthogonally oriented posture sensors 40.

When sensors 40 include accelerometers, for example, that are aligned in this manner, processor 46 may monitor the magnitude and polarity of DC components of the signals generated by the accelerometers to determine the orientation of a patient 12 relative to the Earth's gravity, e.g., the posture of the patient 12. In particular, the processor 46 may compare the DC components of the signals to respective threshold values stored in memory 48 to determine whether a patient 12 is or is not recumbent. Further information regarding use of orthogonally aligned accelerometers to determine patient posture may be found in a commonly assigned U.S. Pat. No. 5,593,431, which issued to Todd J. Sheldon. Other sensors 40 that may generate a signal that indicates the posture of a patient 12 include electrodes that generate an electromyogram (EMG) signal, or bonded piezoelectric crystals that generate a signal as a function of contraction of muscles. Such sensors 40 may be implanted in the legs, buttocks, chest, abdomen, or back of a patient 12, as described above. The signals generated by such sensors when implanted in these locations may vary based on the posture of a patient 12, e.g., may vary based on whether the patient is standing, sitting, or laying down.

Further, the posture of a patient 12 may affect the thoracic impedance of the patient. Consequently, sensors 40 may include an electrode pair, including one electrode integrated with the housing of an IMD 14 and one of electrodes 42, that generates a signal as a function of the thoracic impedance of a patient 12, and processor 46 may detect the posture or posture changes of the patient 12 based on the signal. The electrodes of the pair may be located on opposite sides of the patient's thorax. For example, the electrode pair may include one of electrodes 42 located proximate to the spine of a patient for delivery of SCS therapy, and an IMD 14 with an electrode integrated in its housing may be implanted in the abdomen of a patient 12.

Additionally, changes of the posture of a patient 12 may cause pressure changes with the cerebrospinal fluid (CSF) of the patient. Consequently, sensors 40 may include pressure sensors coupled to one or more intrathecal or intracerebroventricular catheters, or pressure sensors coupled to an IMD 14 wirelessly or via a lead 16. CSF pressure changes associated with posture changes may be particularly evident within the brain of the patient, e.g., may be particularly apparent in an intracranial pressure (ICP) waveform.

In some embodiments, processor 46 considers both the posture and the activity level of a patient 12 when determining whether the patient 12 is attempting to fall asleep. For example, processor 46 may determine whether a patient 12 is attempting to fall asleep based on a sufficiently long period of sub-threshold activity, as described above, and may identify the time that patient began attempting to fall asleep as the time when a patient 12 became recumbent. Any of a variety of combinations or variations of these techniques may be used to determine when a patient 12 is attempting to fall asleep, and a specific one or more techniques may be selected based on the sleeping and activity habits of a particular patient.

In other embodiments, processor 46 determines when a patient 12 is attempting to fall asleep based on the level of melatonin in a bodily fluid. In such embodiments, a sensor 40 may take the form of a chemical sensor that is sensitive to the level of melatonin or a metabolite of melatonin in the bodily fluid, and estimate the time that a patient 12 will attempt to fall asleep based on the detection. For example, processor 46 may compare the melatonin level or rate of change in the melatonin level to a threshold level stored in memory 48, and identify the time that threshold value is exceeded. Processor 46 may identify the time that patient a 12 is attempting to fall asleep as the time that the threshold is exceeded, or some amount of time after the threshold is exceeded. Any of a variety of combinations or variations of the above-described techniques may be used to determine when a patient 12 is attempting to fall asleep, and a specific one or more techniques may be selected based on the sleeping and activity habits of a particular patient.

Processor 46 may also determine when a patient 12 is asleep, e.g., identify the times that the patient 12 falls asleep and wakes up, in order to determine one or more sleep quality metric values. The detected values of physiological parameters of a patient 12, such as activity level, heart rate, ECG morphological features, EEG morphological features, respiration rate, respiratory volume, blood pressure, blood oxygen saturation, partial pressure of oxygen within blood, partial pressure of oxygen within cerebrospinal fluid, muscular activity and tone, core temperature, subcutaneous temperature, arterial blood flow, brain electrical activity, eye motion, and galvanic skin response may discernibly change when a patient 12 falls asleep or wakes up. Some of these physiological parameters may be at low values when a patient 12 is asleep. Further, the variability of at least some of these parameters, such as heart rate and respiration rate, may be at a low value when the patient is asleep.

Consequently, in order to detect when a patient 12 falls asleep and wakes up, processor 46 may monitor one or more of these physiological parameters, or the variability of these physiological parameters, and detect the discernable changes in their values associated with a transition between a sleeping state and an awake state. In some embodiments, processor 46 may determine a mean or median value for a parameter based on values of a signal over time, and determine whether a patient 12 is asleep or awake based on the mean or median value. Processor 46 may compare one or more parameter or parameter variability values to thresholds stored in memory 48 to detect when a patient 12 falls asleep or awakes. The thresholds may be absolute values of a physiological parameter, or time rate of change values for the physiological parameter, e.g., to detect sudden changes in the value of a parameter or parameter variability. In some embodiments, a threshold used by processor 46 to determine whether a patient 12 is asleep may include a time component. For example, a threshold may require that a physiological parameter be above or below a threshold value for a period of time before processor 46 determines that patient is awake or asleep.

In some embodiments, in order to determine whether a patient 12 is asleep, processor 46 monitors a plurality of physiological parameters, and determines a value of a metric that indicates the probability that the patient 12 is asleep for each of the parameters based on a value of the parameter. In particular, the processor 46 may apply a function or look-up table to the current, mean or median value, and/or the variability of each of a plurality of physiological parameters to determine a sleep probability metric value for each of the plurality of physiological parameters. A sleep probability metric value may be a numeric value, and in some embodiments may be a probability value, e.g., a number within the range from 0 to 1, or a percentage level.

Processor 46 may average or otherwise combine the plurality of sleep probability metric values to provide an overall sleep probability metric value. In some embodiments, processor 46 may apply a weighting factor to one or more of the sleep probability metric values prior to combination. Processor 46 may compare the overall sleep probability metric value to one or more threshold values stored in memory 48 to determine when a patient 12 falls asleep or awakes. Use of sleep probability metric values to determine when a patient is asleep based on a plurality of monitored physiological parameters is described in greater detail in a commonly-assigned and copending U.S. patent application Ser. No. 11/691,405, by Ken Heruth and Keith Miesel, entitled "DETECTING SLEEP," which was assigned and filed on Mar. 26, 2007, and is incorporated herein by reference in its entirety.

To enable processor 46 to determine when a patient 12 is asleep or awake, sensors 40 may include, for example, activity sensors as described above. In some embodiments, the activity sensors may include electrodes or bonded piezoelectric crystals, which may be implanted in the back, chest, buttocks, or abdomen of a patient 12 as described above. In such embodiments, processor 46 may detect the electrical activation and contractions of muscles associated with gross motor activity of the patient, e.g., walking, running or the like via the signals generated by such sensors. Processor 46 may also detect spasmodic, irregular, movement disorder or pain related muscle activation via the signals generated by such sensors. Such muscle activation may indicate that a patient 12 is not sleeping, e.g., unable to sleep, or if the patient 12 is sleeping, may indicate a lower level of sleep quality.

As another example, sensors 40 may include electrodes located on leads or integrated as part of the housing of an IMD 14 that output an electrogram signal as a function of electrical activity of the heart of a patient 12, and processor 46 may monitor the heart rate of the patient 12 based on the electrogram signal. In other embodiments, a sensor may include an acoustic sensor within an IMD 14, a pressure sensor within the bloodstream or cerebrospinal fluid of a patient 12, or a temperature sensor located within the bloodstream of the patient 12. The signals output by such sensors may vary as a function of contraction of the heart of a patient 12, and can be used by an IMD 14 to monitor the heart rate of the patient 12.

In some embodiments, processor 46 may detect, and measure values for one or more ECG morphological features within an electrogram generated by electrodes as described above. ECG morphological features may vary in a manner that indicates whether a patient 12 is asleep or awake. For example, the amplitude of the ST segment of the ECG may decrease when a patient 12 is asleep. Further, the amplitude of QRS complex or T-wave may decrease, and the widths of the QRS complex and T-wave may increase when a patient 12 is asleep. The QT interval and the latency of an evoked response may increase when a patient 12 is asleep, and the amplitude of the evoked response may decrease when the patient 12 is asleep.

In some embodiments, sensors 40 may include an electrode pair, including one electrode integrated with the housing of an IMD 14 and one of electrodes 42, that outputs a signal as a function of the thoracic impedance of the patient 12, as described above, which varies as a function of respiration by the patient 12. In other embodiments, sensors 40 may include a strain gage, bonded piezoelectric element, or pressure sensor within the blood or cerebrospinal fluid that outputs a signal that varies based on patient respiration. An electrogram output by electrodes as discussed above may also be modulated by patient respiration, and may be used as an indirect representation of respiration rate.

Sensors 40 may include electrodes that output an electromyogram (EMG) signal as a function of muscle electrical activity, as described above, or may include any of a variety of known temperature sensors to output a signal as a function of a core or subcutaneous temperature of a patient 12. Such electrodes and temperature sensors may be incorporated within the housing of an IMD 14, or coupled to the IMD 14 wirelessly or via leads. Sensors 40 may also include a pressure sensor within, or in contact with, a blood vessel. The pressure sensor may output a signal as a function of the a blood pressure of a patient 12, and may, for example, comprise a Chronicle Hemodynamic Monitor™ commercially available from Medtronic, Inc. of Minneapolis, Minn. Further, certain muscles of a patient 12, such as the muscles of the patient's neck, may discernibly relax when the patient 12 is asleep or within certain sleep states. Consequently, sensors 40 may include strain gauges or EMG electrodes implanted in such locations that generate a signal as a function of muscle tone.

Sensors 40 may also include optical pulse oximetry sensors or Clark dissolved oxygen sensors located within, as part of a housing of, or outside of an IMD 14, which output signals as a function of blood oxygen saturation and blood oxygen partial pressure respectively. In some embodiments, systems 10 may include a catheter with a distal portion located within the cerebrospinal fluid of a patient 12, and the distal end may include a Clark sensor to output a signal as a function of the partial pressure of oxygen within the cerebrospinal fluid. Embodiments in which an IMD comprises an implantable pump, for example, may include a catheter with a distal portion located in the cerebrospinal fluid.

In some embodiments, sensors 40 may include one or more intraluminal, extraluminal, or external flow sensors positioned to output a signal as a function of arterial blood flow. A flow sensor may be, for example, and electromagnetic, thermal convection, ultrasonic-Doppler, or laser-Doppler flow sensor. Further, in some external medical device embodiments of the invention, sensors 40 may include one or more electrodes positioned on the skin of a patient 12 to output a signal as a function of galvanic skin response.

Additionally, in some embodiments, sensors 40 may include one or more electrodes positioned within or proximate to the brain of patient, which detect electrical activity of the brain. For example, in embodiments in which an IMD 14 delivers stimulation or other therapy to the brain, processor 46 may be coupled to electrodes implanted on or within the brain via a lead 16. System 10B, illustrated in FIGS. 1B and 2B, is an example of a system that includes electrodes 42, located on or within the brain of patient 12B, that are coupled to IMD 14B.

As shown in FIG. 2B, electrodes 42 may be selectively coupled to therapy module 44 or an EEG signal module 54 by a multiplexer 52, which operates under the control of processor 46. EEG signal module 54 receives signals from a selected set of the electrodes 42 via multiplexer 52 as controlled by processor 46. EEG signal module 54 may analyze the EEG signal for certain features indicative of sleep or different sleep states, and provide indications of relating to sleep or sleep states to processor 46. Thus, electrodes 42 and EEG signal module 54 may be considered another sensor 40 in system 10B. IMD 14B may include circuitry (not shown) that conditions the EEG signal such that it may be analyzed by processor 52. For example, IMD 14B may include one or more analog to digital converters to convert analog signals received from electrodes 42 into digital signals usable by processor 46, as well as suitable filter and amplifier circuitry.

In some embodiments, processor 46 will only request EEG signal module 54 to operate when one or more other physiological parameters indicate that patient 12B is already asleep. However, processor 46 may also direct EEG signal module to analyze the EEG signal to determine whether patient 12B is sleeping, and such analysis may be considered alone or in combination with other physiological parameters to determine whether patient 12B is asleep. EEG signal module 60 may process the EEG signals to detect when patient 12 is asleep using any of a variety of techniques, such as techniques that identify whether a patient is asleep based on the amplitude and/or frequency of the EEG signals. In some embodiments, the functionality of EEG signal module 54 may be provided by processor 46, which, as described above, may include one or more microprocessors, ASICs, or the like.

In other embodiments, processor 46 may be wirelessly coupled to electrodes that detect brain electrical activity. For example, one or more modules may be implanted beneath the scalp of the patient, each module including a housing, one or more electrodes, and circuitry to wirelessly transmit the signals detected by the one or more electrodes to an IMD 14. In other embodiments, the electrodes may be applied to the patient's scalp, and electrically coupled to a module that includes circuitry for wirelessly transmitting the signals detected by the electrodes to an IMD 14. The electrodes may be glued to the patient's scalp, or a head band, hair net, cap, or the like may incorporate the electrodes and the module, and may be worn by a patient 12 to apply the electrodes to the patient's scalp when, for example, the patient is attempting to sleep. The signals detected by the electrodes and transmitted to an IMD 14 may be electroencephalogram (EEG) signals, and processor 46 may process the EEG signals to detect when a patient 12 is asleep using any of a variety of known techniques, such as techniques that identify whether a patient is asleep based on the amplitude and/or frequency of the EEG signals.

Also, the motion of the eyes of a patient 12 may vary depending on whether the patient is sleeping and which sleep state the patient is in. Consequently, sensors 40 may include electrodes place proximate to the eyes of a patient 12 to detect electrical activity associated with motion of the eyes, e.g., to generate an electro-oculography (EOG) signal. Such electrodes may be coupled to an IMD 14 via one or more leads 16, or may be included within modules that include circuitry to wirelessly transmit detected signals to the IMD 14. Wirelessly coupled modules incorporating electrodes to detect eye motion may be worn externally by a patient 12, e.g., attached to the skin of a patient 12 proximate to the eyes by an adhesive when the patient is attempting to sleep.

Processor 46 may also detect arousals and/or apneas that occur when a patient 12 is asleep based on one or more of the above-identified physiological parameters. For example, processor 46 may detect an arousal based on an increase or sudden increase in one or more of heart rate, heart rate variability, respiration rate, respiration rate variability, blood pressure, or muscular activity as the occurrence of an arousal. Processor 46 may detect an apnea based on a disturbance in the respiration rate of a patient 12, e.g., a period with no respiration.

Processor 46 may also detect arousals or apneas based on sudden changes in one or more of the ECG morphological features identified above. For example, a sudden elevation of the ST segment within the ECG may indicate an arousal or an apnea. Further, sudden changes in the amplitude or frequency of an EEG signal, EOG signal, or muscle tone signal may indicate an apnea or arousal. Memory 48 may store thresholds used by processor 46 to detect arousals and apneas. Processor 46 may determine, as a sleep quality metric value, the number of apnea events and/or arousals during a night.

Further, in some embodiments, processor 46 may determine which sleep state a patient 12 is in during sleep, e.g., REM, S1, S2, S3, or S4, based on one or more of the monitored physiological parameters. In some embodiments, memory 48 may store one or more thresholds for each of sleep states, and processor 46 may compare physiological parameter or sleep probability metric values to the thresholds to determine which sleep state a patient 12 is currently in. Further, in some embodiments, processor 46 and/or EEG signal module 54 may use any of a variety of known techniques for determining which sleep state patient is in based on an EEG signal, which processor 46 and/or EEG signal module may receive via electrodes as described above, such as techniques that identify sleep state based on the amplitude and/or frequency of the EEG signals. In some embodiments, processor 46 may also determine which sleep state patient is in based on an EOG signal, which processor 46 may receive via electrodes as described above, either alone or in combination with an EEG signal, using any of a variety of techniques known in the art. Processor 46 may determine, as sleep quality metric values, the amounts of time per night spent in the various sleep states. As discussed above, inadequate time spent in deeper sleep states, e.g., S3 and S4, is an indicator of poor sleep quality. Consequently, in some embodiments, processor 46 may determine an amount or percentage of time spent in one or both of the S3 and S4 sleep states as a sleep quality metric.

Figure 3:
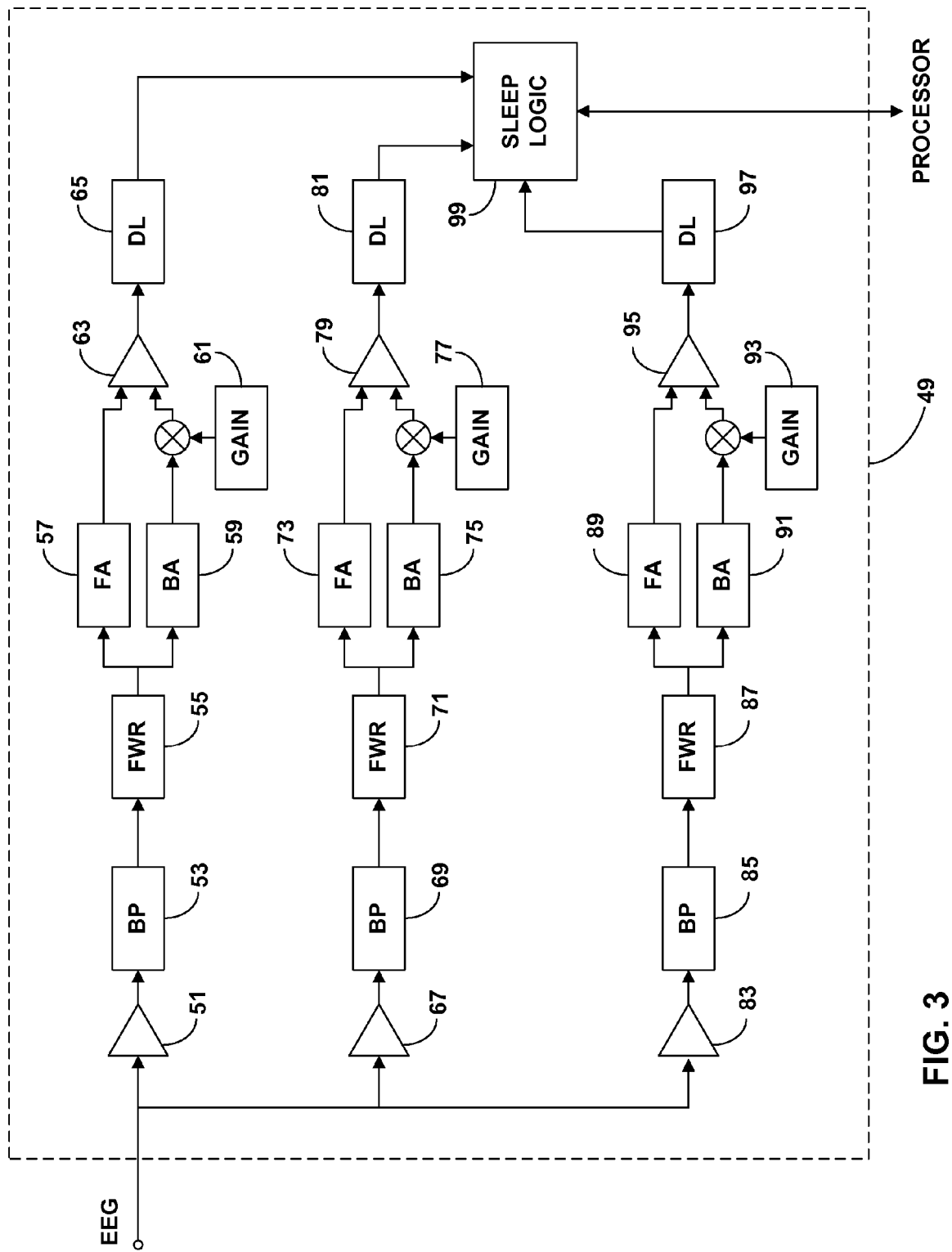
FIG. 3 is a logic diagram illustrating an example circuit that detects the sleep state of a patient from the electroencephalogram (EEG) signal.

FIG. 3 is a logical diagram of an example circuit that detects sleep and/or the sleep type of a patient based on the electroencephalogram (EEG) signal. Alternatively, the circuit may determine an awake state when a patient 12 is not in a sleep state. As shown in FIG. 3, module 49 may be integrated into an EEG signal module of an IMD 14 or a separate implantable or external device capable of detecting an EEG signal. An EEG signal detected by electrodes adjacent to the brain of a patent 12 is transmitted into module 49 and provided to three channels, each of which includes a respective one of amplifiers 51, 67 and 83, and bandpass filters 53, 69 and 85. In other embodiments, a common amplifier amplifies the EEG signal prior to filters 53, 69 and 85.

Bandpass filter 53 allows frequencies between approximately 4 Hz and approximately 8 Hz, and signals within the frequency range may be prevalent in the EEG during S1 and S2 sleep states. Bandpass filter 69 allows frequencies between approximately 1 Hz and approximately 3 Hz, which may be prevalent in the EEG during the S3 and S4 sleep states. Bandpass filter 85 allows frequencies between approximately 10 Hz and approximately 50 Hz, which may be prevalent in the EEG during REM sleep. Each resulting signal may then be processed to identify the current sleep state of a patient 12.

After bandpass filtering of the original EEG signal, the filtered signals are similarly processed in parallel before being delivered to sleep logic module 99. For ease of discussion, only one of the three channels will be discussed herein, but each of the filtered signals would be processed similarly.

Once the EEG signal is filtered by bandpass filter 53, the signal is rectified by full-wave rectifier 55. Modules 57 and 59 respectively determine the foreground average and background average so that the current energy level can be compared to a background level at comparator 63. The signal from background average is increased by gain 61 before being sent to comparator 63, because comparator 63 operates in the range of millivolts or volts while the EEG signal amplitude is originally on the order of microvolts. The signal from comparator 63 is indicative of sleep stages S1 and S2. If duration logic 65 determines that the signal is greater than a predetermined level for a predetermined amount of time, the signal is sent to sleep logic module 99 indicating that a patient 12 may be within the S1 or S2 sleep states. In some embodiments, as least duration logic 65, 81, 97 and sleep logic 99 may be embodied in a processor of the device containing EEG module 49.

Module 49 may detect all sleep types for a patient 12. Further, the beginning of sleep may be detected by module 49 based on the sleep state of a patient 12. Some of the components of module 49 may vary from the example of FIG. 3. For example, gains 61, 77 and 93 may be provided from the same power source. Module 49 may be embodied as analog circuitry, digital circuitry, or a combination thereof.

In other embodiments, FIG. 3 may not need to reference the background average to determine the current state of sleep of a patient 12. Instead, the power of the signals from bandpass filters 53, 69 and 85 are compared to each other, and sleep logic module 99 determines which the sleep state of patient 12 based upon the frequency band that has the highest power. In this case, the signals from full-wave rectifiers 55, 71 and 87 are sent directly to a device that calculates the signal power, such as a spectral power distribution module (SPD), and then to sleep logic module 99 which determines the frequency band of the greatest power, e.g., the sleep state of a patient 12. In some cases, the signal from full-wave rectifiers 55, 71 and 87 may be normalized by a gain component to correctly weight each frequency band.

Figure 4:
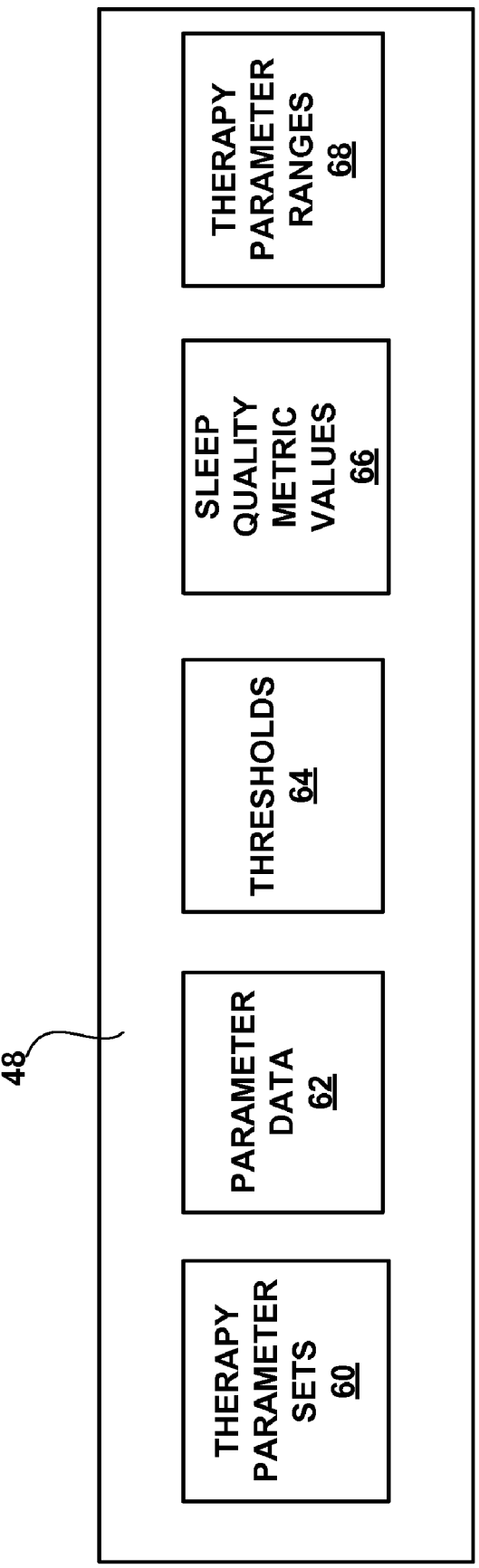
FIG. 4 is a block diagram illustrating an example memory of the implantable medical device of FIGS. 1A and 1B.

FIG. 4 further illustrates memory 48 of an IMD 14. As illustrated in FIG. 4, memory 48 stores a plurality of therapy parameter sets 60. Therapy parameter sets 60 may include parameter sets specified by a clinician using clinician programmer 20. Therapy parameter sets 60 may also include parameter sets that are the result of a patient 12 changing one or more parameters of one of the preprogrammed therapy parameter sets via patient programmer 26.

Memory 48 may also include parameter information 60 recorded by processor 46, e.g., physiological parameter values, or mean or median physiological parameter values. Memory 48 stores threshold values 64 used by processor 46 in the collection of sleep quality metric values, as discussed above. In some embodiments, memory 48 also stores one or more functions or look-up tables (not shown) used by processor 46 to determine sleep probability metric values, or to determine an overall sleep quality metric value.

Further, processor 46 stores determined values 66 for one or more sleep quality metrics within memory 48. Processor 46 may collect sleep quality metric values 66 each time a patient 12 sleeps, or only during selected times that the patient 12 is asleep. Processor 46 may store each sleep quality metric value determined within memory 48 as a sleep quality metric value 66, or may store mean or median sleep quality metric values over periods of time such as weeks or months as sleep quality metric values 66. Further, processor 46 may apply a function or look-up table to a plurality of sleep quality metric values to determine overall sleep quality metric value, and may store the overall sleep quality metric values within memory 48. The application of a function or look-up table by processor 46 for this purpose may involve the use or weighting factors for one or more of the individual sleep quality metric values.

In some embodiments, processor 46 identifies which of therapy parameter sets 60 is currently selected for use in delivering therapy to a patient 12 when a value of one or more sleep quality metrics is collected, and may associate that value with the current parameter set. For example, for each available therapy parameter set 60, processor 46 may store a representative value of each of one or more sleep quality metrics within memory 48 as a sleep quality metric value 66 with an indication of which therapy parameter set that representative value is associated with. A representative value of sleep quality metric for a therapy parameter set may be the mean or median of collected sleep quality metric values that have been associated with that parameter set.

In some embodiments, as discussed above, processor 46 may adjust the intensity of the therapy delivered by therapy module 44 based on one or more sleep quality metric values 66. In particular, processor 46 may adjust one or more therapy parameters, such as pulse amplitude, pulse width, pulse rate, and duty cycle to adjust the intensity of the stimulation. In some embodiments, memory 48 may store parameter ranges 68 specified by a clinician or the manufacturer of an IMD 14, and processor 46 may adjust parameters within the specified ranges.

In some embodiments, processor 46 may iteratively and incrementally increase the intensity so long as the comparison indicates poor sleep quality. In other embodiments, processor 46 may substantially increase the intensity of the therapy when the comparison indicates poor sleep quality in order to more quickly identify an efficacious operating point. In some embodiments, processor 46 may gradually decrease the intensity of the therapy so long as the comparison indicates that the sleep quality experienced by a patient 12 is adequate to, for example, conserve the energy stored by a battery of an IMD 14. In other embodiments, the amount by which processor 46 increases or decreases the intensity of therapy may be proportional to the difference or ratio between the current sleep quality metric value and a threshold value.

Figure 5:
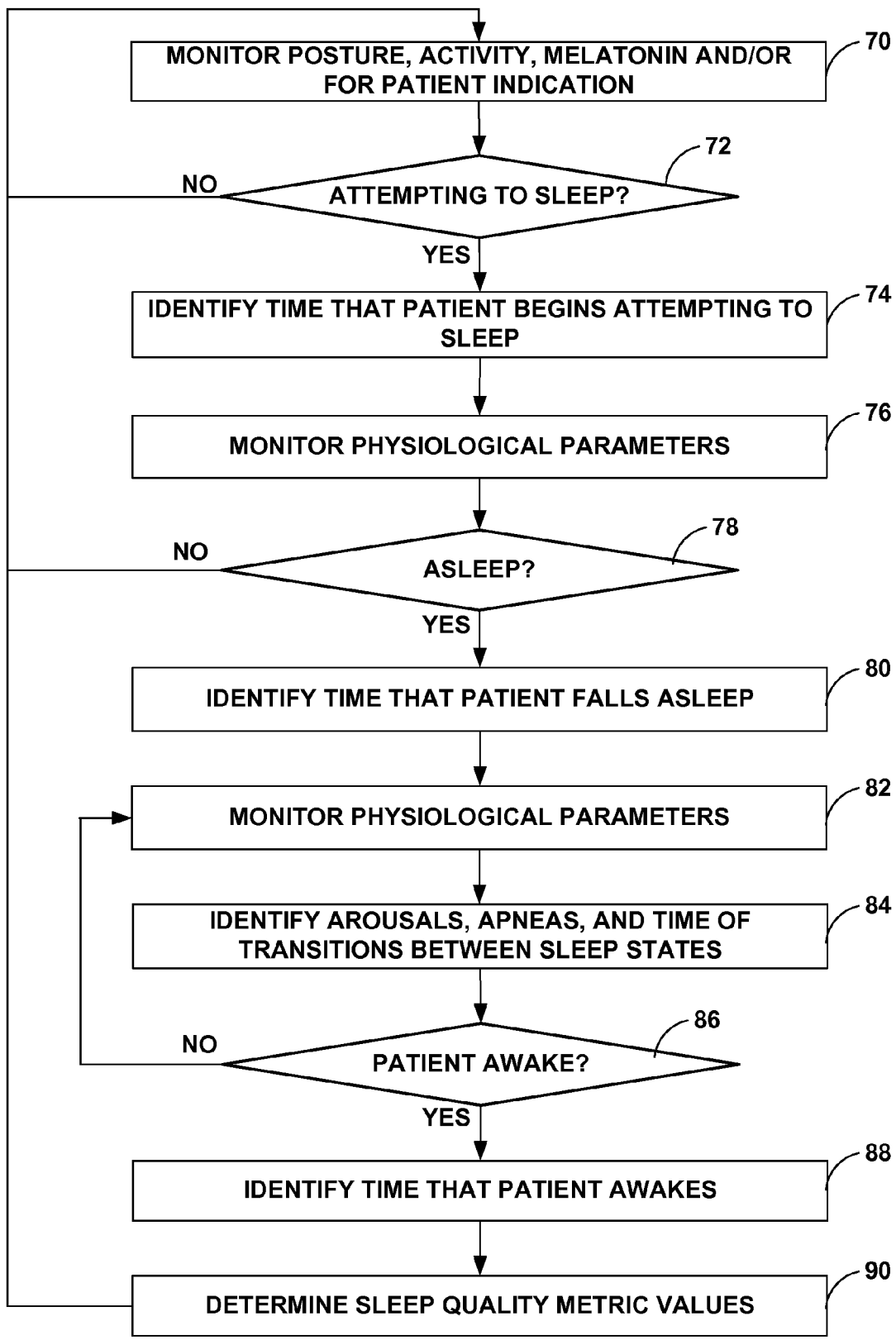
FIG. 5 is a flow diagram illustrating an example method for collecting sleep quality information that may be employed by an implantable medical device.

FIG. 5 is a flow diagram illustrating an example method for collecting sleep quality information that may be employed by an IMD 14. An IMD 14 monitors the posture, activity level, and/or melatonin level of a patient 12, or monitors for an indication from the patient 12, e.g., via patient programmer 26 (70), and determines whether the patient 12 is attempting to fall asleep based on the posture, activity level, melatonin level, and/or a patient indication, as described above (72). If an IMD 14 determines that a patient 12 is attempting to fall asleep, the IMD 14 identifies the time that the patient 12 began attempting to fall asleep using any of the techniques described above (74), and monitors one or more of the various physiological parameters of the patient 12 discussed above to determine whether the patient 12 is asleep (76, 78).

In some embodiments, an IMD 14 compares parameter values or parameter variability values to one or more threshold values 64 to determine whether a patient 12 is asleep. In other embodiments, an IMD 14 applies one or more functions or look-up tables to determine one or more sleep probability metric values based on the physiological parameter values, and compares the sleep probability metric values to one or more threshold values 64 to determine whether a patient 12 is asleep. While monitoring physiological parameters (76) to determine whether a patient 12 is asleep (78), an IMD 14 may continue to monitor the posture and/or activity level of the patient 12 (70) to confirm that the patient 12 is still attempting to fall asleep (72).

When an IMD 14 determines that a patient 12 is asleep, e.g., by analysis of the various parameters contemplated herein, the IMD 14 will identify the time that the patient 12 fell asleep (80). While a patient 12 is sleeping, an IMD 14 will continue to monitor physiological parameters of the patient 12 (82). As discussed above, an IMD 14 may identify the occurrence of arousals and/or apneas based on the monitored physiological parameters (84). Further, an IMD 14 may identify the time that transitions between sleep states, e.g., REM, S1, S2, S3, and S4, occur based on the monitored physiological parameters (84).

Additionally, while a patient 12 is sleeping, an IMD 14 monitors physiological parameters of the patient 12 (82) to determine whether the patient 12 has woken up (86). When an IMD 14 determines that a patient 12 is awake, the IMD 14 identifies the time that the patient 12 awoke (88), and determines sleep quality metric values based on the information collected while the patient 12 was asleep (90).

For example, one sleep quality metric value an IMD 14 may calculate is sleep efficiency, which the IMD 14 may calculate as a percentage of time during which a patient 12 is attempting to sleep that the patient 12 is actually asleep. An IMD 14 may determine a first amount of time between the time the IMD 14 identified that a patient 12 fell asleep and the time the IMD 14 identified that the patient 12 awoke. An IMD 14 may also determine a second amount of time between the time the IMD 14 identified that a patient 12 began attempting to fall asleep and the time the IMD 14 identified that the patient 12 awoke. To calculate the sleep efficiency, an IMD 14 may divide the first time by the second time.

Another sleep quality metric value that an IMD 14 may calculate is sleep latency, which the IMD 14 may calculate as the amount of time between the time the IMD 14 identified that a patient 12 was attempting to fall asleep and the time the IMD 14 identified that the patient 12 fell asleep. Other sleep quality metrics with values determined by an IMD 14 based on the information collected by the IMD 14 in the illustrated example include: total time sleeping per day, at night, and during daytime hours; number of apnea and arousal events per occurrence of sleep; and amount of time spent in the various sleep states, e.g., one or both of the S3 and S4 sleep states. An IMD 14 may store the determined values as sleep quality metric values 66 within memory 48.

An IMD 14 may perform the example method illustrated in FIG. 5 continuously, e.g., may monitor to identify when a patient 12 is attempting to sleep and asleep any time of day, each day. In other embodiments, an IMD 14 may only perform the method during evening hours and/or once every N days to conserve battery and memory resources. Further, in some embodiments, an IMD 14 may only perform the method in response to receiving a command from a patient 12 or a clinician via one of programmers 20, 26. For example, a patient 12 may direct an IMD 14 to collect sleep quality information at times when the patient believes that his or her sleep quality is low or therapy is ineffective.

Figure 6:
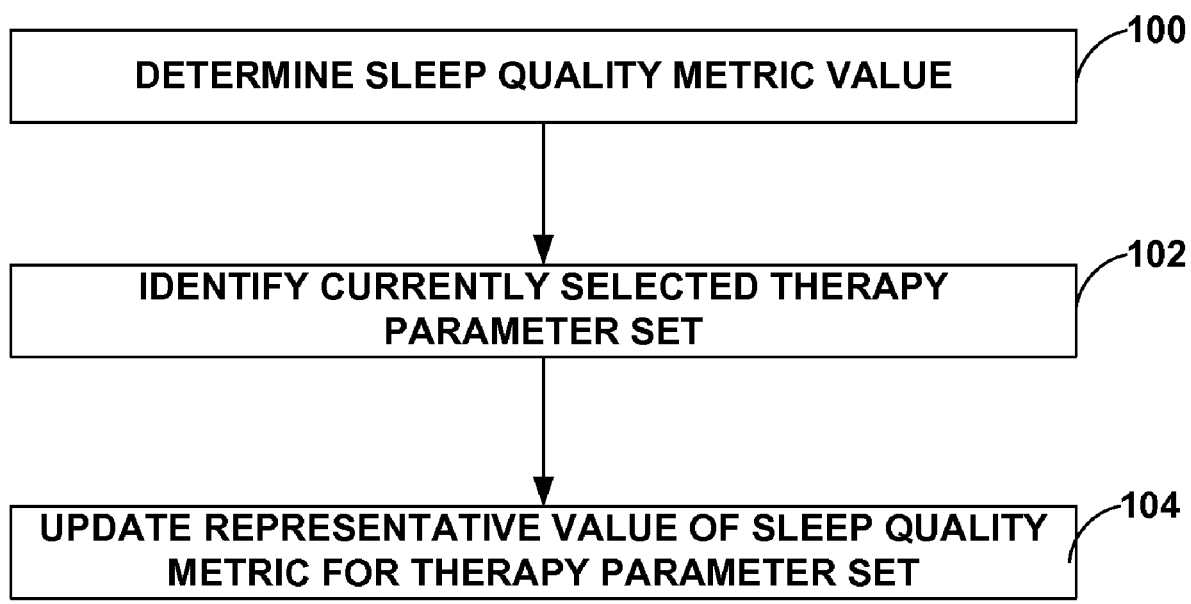
FIG. 6 is a flow diagram illustrating an example method for associating sleep quality information with therapy parameter sets that may be employed by a medical device.

FIG. 6 is a flow diagram illustrating an example method for associating sleep quality information with therapy parameter sets 60 that may be employed by an IMD 14. An IMD 14 determines a value of a sleep quality metric according to any of the techniques described above (100). The IMD 14 also identifies the current therapy parameter set, e.g., the therapy parameter set 60 used by the IMD 14 to control delivery of therapy when a patient 12 was asleep (102), and associates the newly determined value with the current therapy parameter set 60.

Among sleep quality metric values 66 within memory 48, an IMD 14 stores a representative value of the sleep quality metric, e.g., a mean or median value, for each of the plurality of therapy parameter sets 60. An IMD 14 updates the representative values for the current therapy parameter set based on the newly determined value of the sleep quality metric. For example, a newly determined sleep efficiency value may be used to determine a new average sleep efficiency value for the current therapy parameter set 60.

Figure 7:
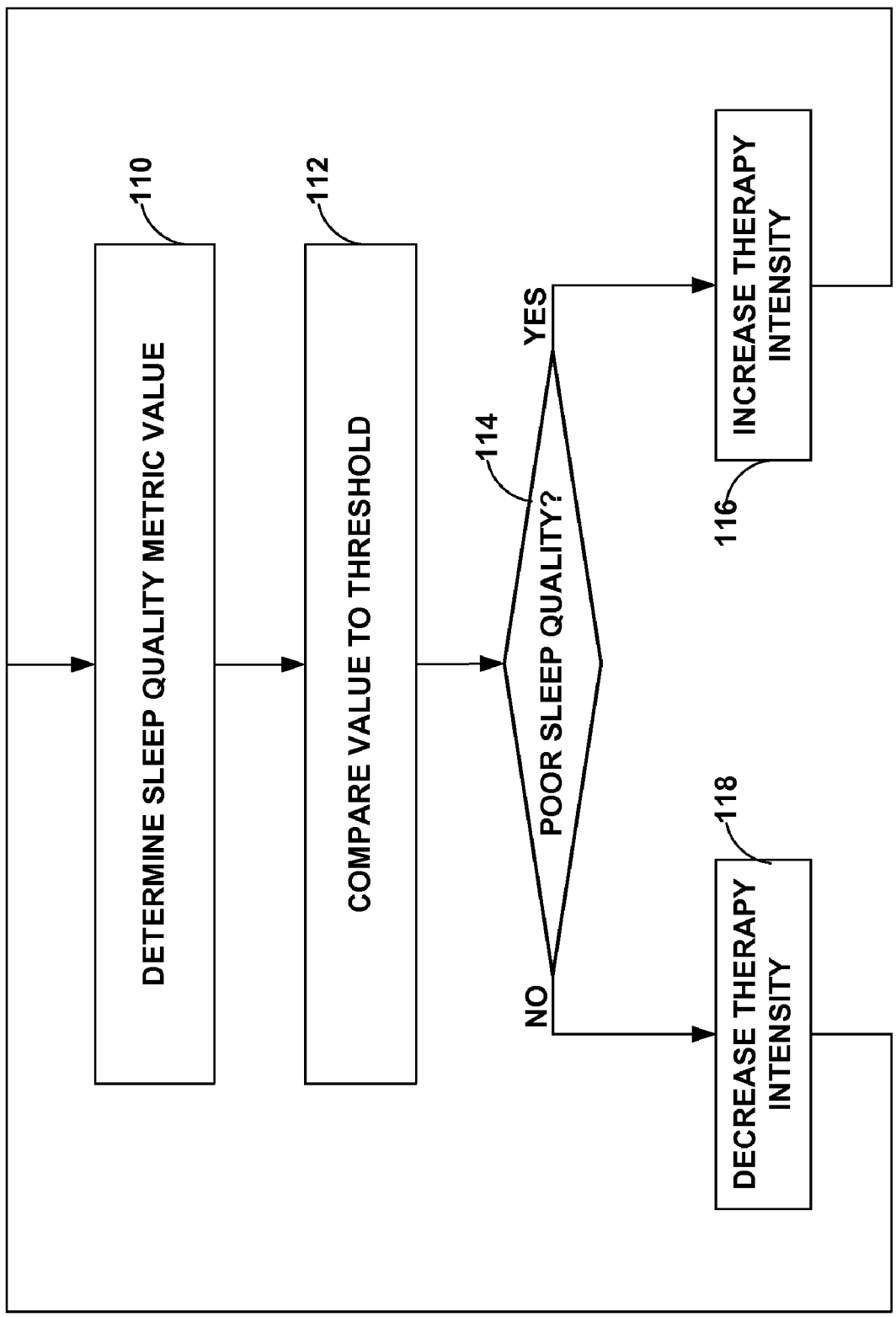
FIG. 7 is a flow diagram illustrating an example method for controlling therapy based on sleep quality information that may be employed by a medical device.

FIG. 7 is a flow diagram illustrating an example method for controlling therapy based on sleep quality information that may be employed by an IMD 14. An IMD 14 determines a value 66 of a sleep quality metric according to any of the techniques described above (1110). The sleep quality metric value 66 may be a current value, mean value, median value, or an overall value, as described above.

An IMD 14 compares the value 66 of the sleep quality metric to one or more threshold values (112), and may determine whether the sleep quality experienced by a patient 12 is poor based on the comparison (114). For example, an IMD 14 may determine that the sleep quality is poor if the sleep quality metric value 66 falls below a threshold value, or has decreased by greater than a threshold amount over a period of time. In some embodiments, an IMD 14 may compare values 66 for a plurality of sleep quality metrics to respective thresholds to determine whether a patient 12 is experiencing poor sleep quality.

If a patient 12 is experiencing poor sleep quality, an IMD 14 may increase the intensity of therapy, e.g., increase a pulse amplitude, pulse width, pulse rate, duty cycle, dosage, or infusion rate (116). On the other hand, if the sleep quality is adequate, an IMD 14 may decrease the intensity of the therapy (118). An IMD 14 may adjust the intensity of therapy by adjusting the values of therapy parameters within ranges 68, as discussed above.

An IMD 14 need not increase and decrease the intensity of therapy by the same amount, e.g., at the same rate. For example, an IMD 14 may increase therapy intensity at a greater rate than it decreases therapy intensity to provide a patient 12 more immediate relief when sleep quality is poor, and to avoid frequent reduction of the therapy intensity below a point at which sleep quality begins to decline. When adjusting the intensity of therapy, an IMD 14 may either temporarily or permanently adjust one or more parameters of the currently selected therapy parameter set 60.

In some embodiments, an IMD 14 may iteratively and incrementally increase the intensity so long as the comparison indicates poor sleep quality. In other embodiments, an IMD 14 may substantially increase the intensity of the therapy when the comparison indicates poor sleep quality in order to more quickly identify an efficacious operating point. In some embodiments, an IMD 14 may gradually decrease the intensity of the therapy so long as the comparison indicates that the sleep quality experienced by a patient 12 is adequate to, for example, conserve the energy stored by a battery of the IMD 14. In other embodiments, the amount by which an IMD 14 increases or decreases the intensity of therapy may be proportional to the difference or ratio between the current sleep quality metric value and the threshold value.

Figure 8:
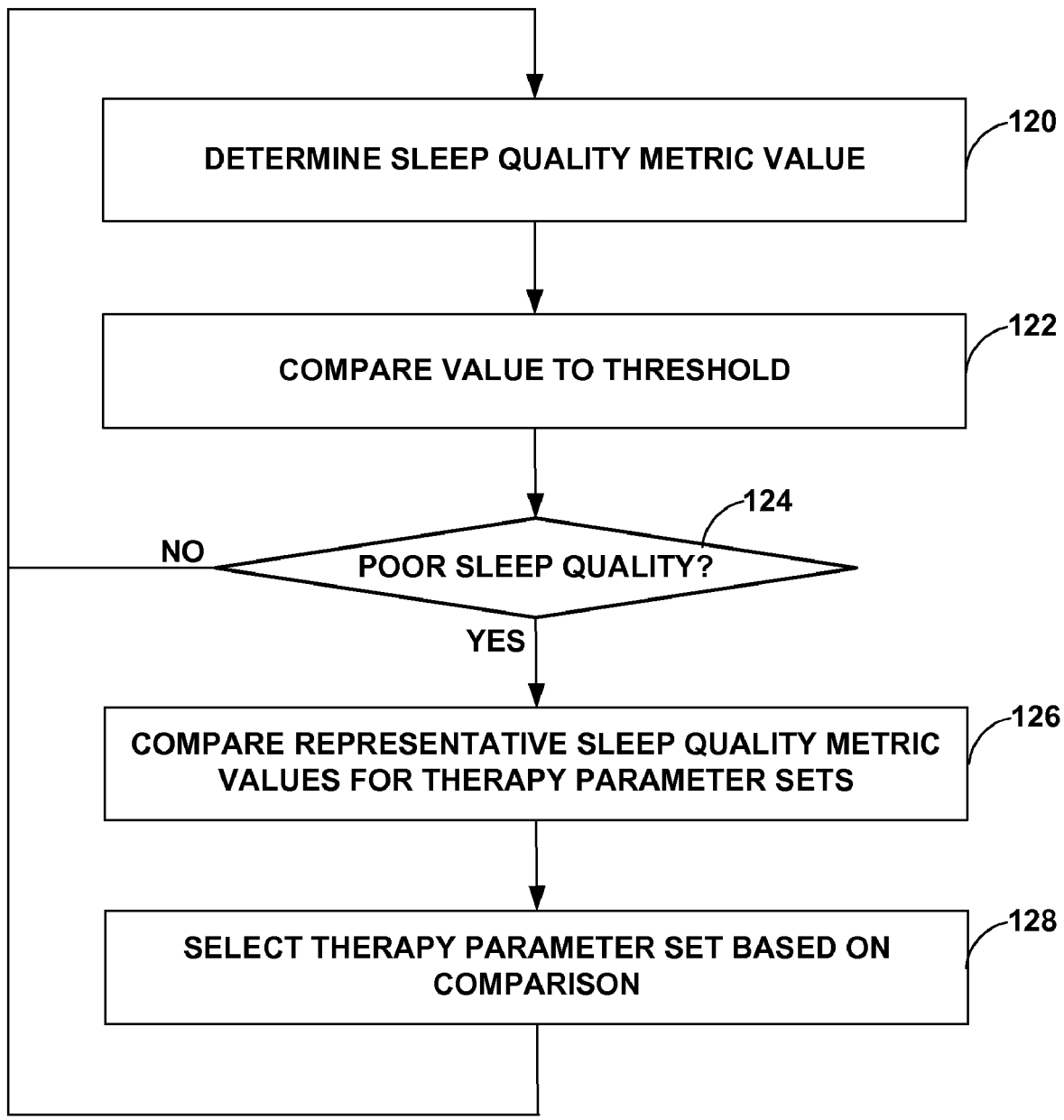
FIG. 8 is a flow diagram illustrating another example method for controlling therapy based on sleep quality information that may be employed by a medical device.

FIG. 8 is a flow diagram illustrating another example method for controlling therapy based on sleep quality information that may be employed by an IMD 14. In particular, FIG. 8 illustrates a method that may be employed by an IMD 14 in embodiments in which the IMD 14 stores associates sleep quality metric values 66 with therapy parameter sets 60, and stores representative values 66 of the sleep quality metrics for the therapy parameter sets 60. An IMD 14 determines a value 66 of a sleep quality metric (120), and compares the value 66 to a threshold 64 (122) to determine whether a patient 12 is experiencing poor sleep quality (124), as described above with reference to FIG. 7.

If the comparison indicates that the sleep quality experienced by a patient 12 is poor, an IMD 14 compares the representative values 66 of the sleep quality metrics (126), and automatically selects one of the therapy parameter sets 60 for use in controlling delivery of therapy based on the comparison (128). An IMD 14 may, for example, select the therapy parameter set 60 with the "best" representative value or values in order to provide the therapy most likely to improve the quality of the patient's sleep. In some embodiments, an IMD 14 may detect subsequent times when a patient 12 is sleeping using the techniques described above, and may automatically activate the selected therapy parameter set at those times. An IMD 14 may use the selected therapy parameter set in this manner for a specified time period, e.g., a number of days, or until a patient 12 overrides the selection via patient programmer 26.

Figure 9:
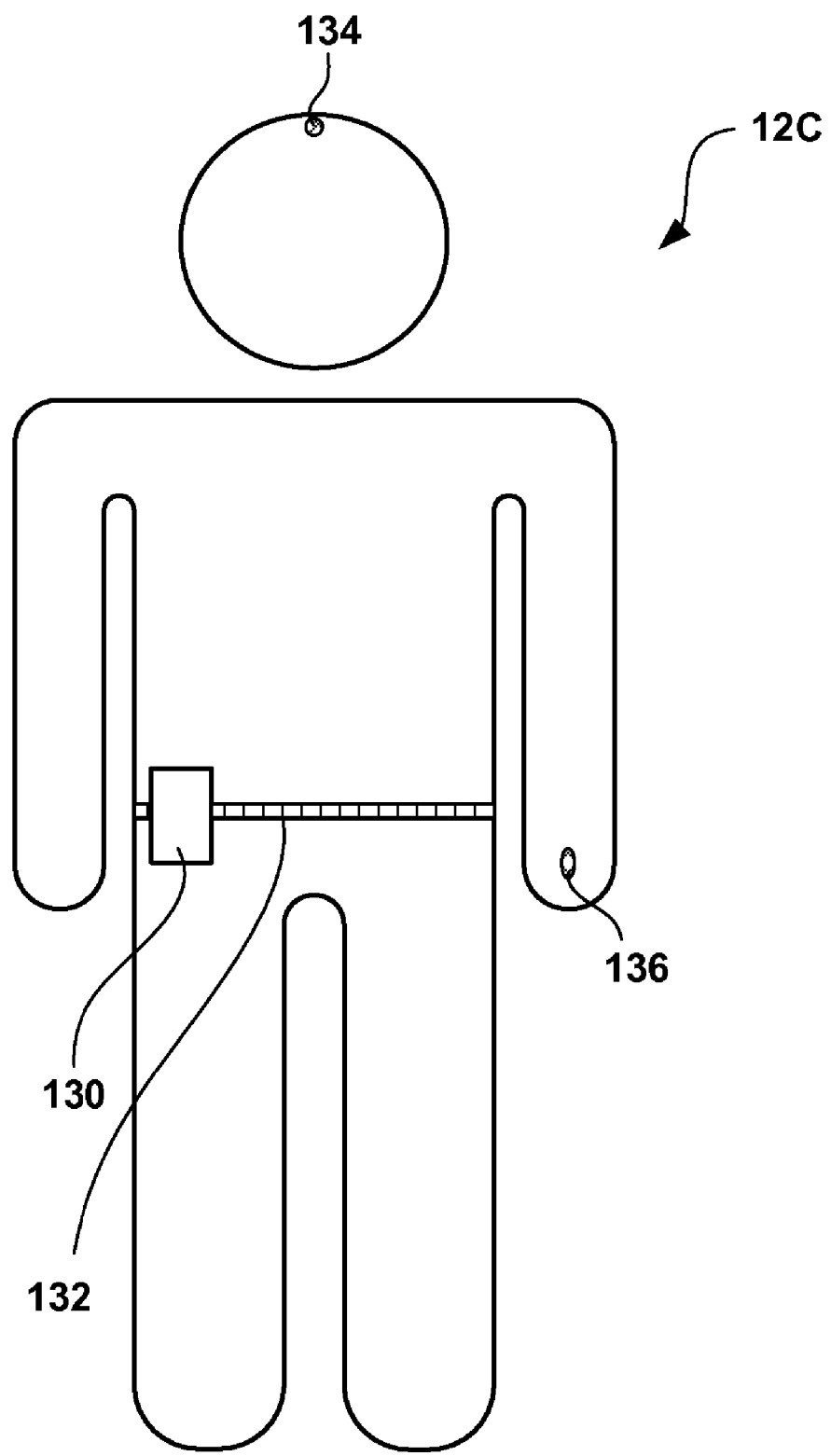
FIG. 9 is a conceptual diagram illustrating a monitor that monitors values of one or more accelerometers of the patient instead of, or in addition to, a therapy delivering medical device.

FIG. 9 is a conceptual diagram illustrating a monitor that monitors values of one or more accelerometers of the patient instead of, or in addition to, such monitoring being performed by a therapy delivering medical device. As shown in FIG. 9, patient 12C is wearing monitor 130 attached to belt 132. Monitor 130 is capable of receiving measurements from one or more sensors located on or within patient 12C. In the example of FIG. 9, accelerometers 134 and 136 are attached to the head and hand of patient 12C, respectively. Accelerometers 134 and 136 may measure movement of the extremities, or activity level, of patient 12C to indicate when the patient moves during sleep or at other times during the day. Alternatively, more or less accelerometers or other sensors may be used with monitor 130.

Accelerometers 134 and 136 may be preferably multi-axis accelerometers, but single-axis accelerometers may be used. As patient 12C moves, accelerometers 134 and 136 detect this movement and send the signals to monitor 130. High frequency movements of patient 12C may be indicative of tremor, Parkinson's disease, or an epileptic seizure, and monitor 130 may be capable of indicating to an IMD 14, for example, that stimulation therapy must be changed to effectively treat the patient. Accelerometers 134 and 136 may be worn externally, i.e., on a piece or clothing or a watch, or implanted at specific locations within patient 12C. In addition, accelerometers 134 and 136 may transmit signals to monitor 130 via wireless telemetry or a wired connection.

Monitor 130 may store the measurements from accelerometers 134 and 136 in a memory. Monitor 130 may analyze the measurements using any of the techniques described herein. In some examples, monitor 146 may transmit the measurements from accelerometers 134 and 136 directly to another device, such as an IMD 14, programming device 20,26, or other computing device. In this case, the other device may analyze the measurements from accelerometers 134 and 136 to detect efficacy of therapy or control the delivery of therapy.

In some examples, a rolling window of time may be used when analyzing measurements from accelerometers 134 and 136. Absolute values determined by accelerometers 134 and 136 may drift with time or the magnitude and frequency of patient 12C movement may not be determined by a preset threshold. For this reason, it may be advantageous to normalize and analyze measurements from accelerometers 134 and 136 over a discrete window of time. For example, the rolling window may be useful in detecting epileptic seizures. If monitor 130 or an IMD 14 detects at least a predetermined number of movements over a 15 second window, an epileptic seizure may be most likely occurring. In this manner, a few quick movements from patient 12C not associated with a seizure may not trigger a response and change in therapy.

Figure 10:
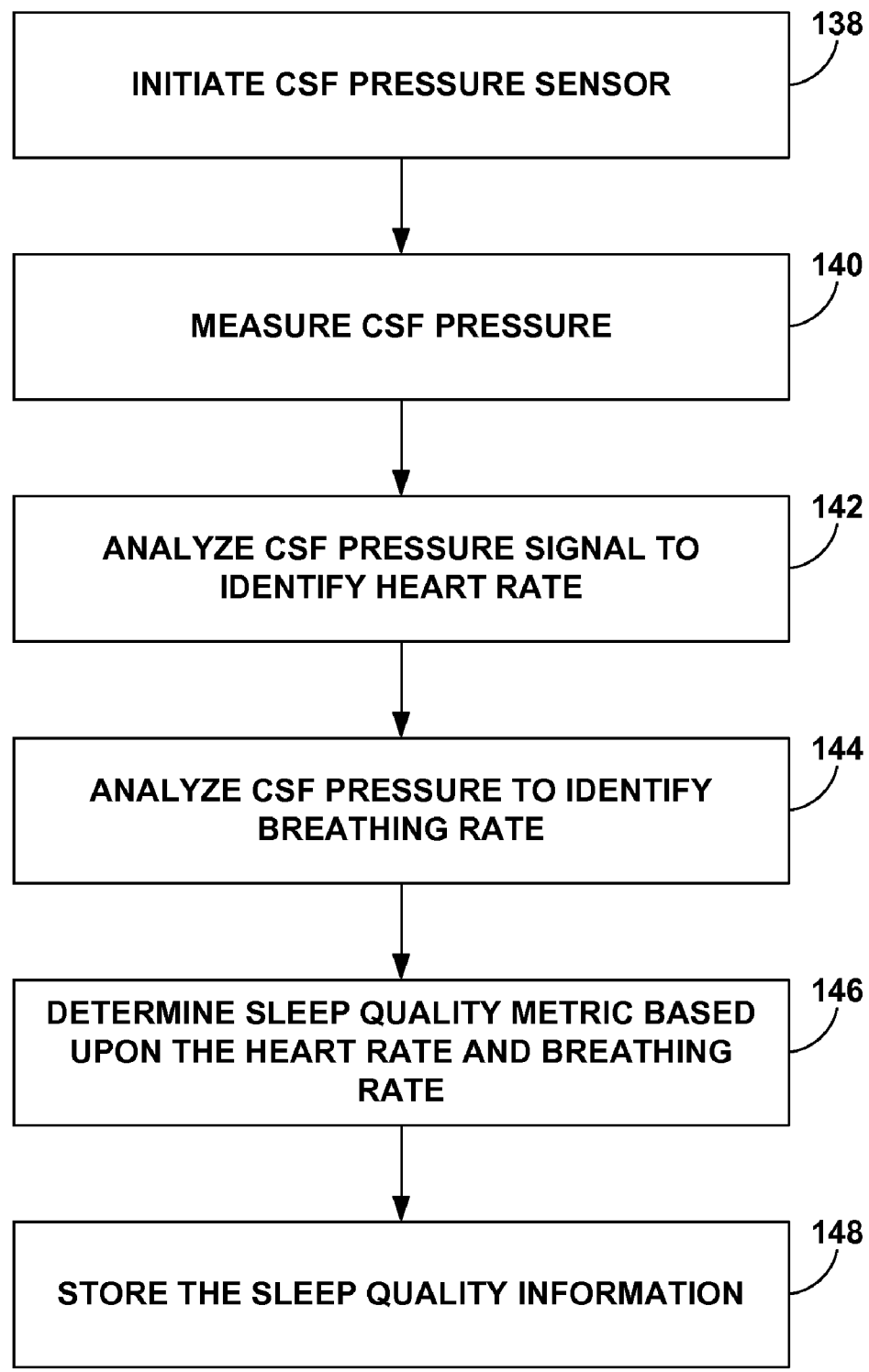
FIG. 10 is a flow diagram illustrating monitoring the heart rate and breathing rate of a patient by measuring cerebral spinal fluid pressure.

FIG. 10 is a flow diagram illustrating monitoring the heart rate and breathing rate of a patient by measuring cerebral spinal fluid pressure. As shown in FIG. 10, a physiological parameter that may be measured in patient 12C is heart rate and respiration, or breathing, rate. Specifically, cerebral spinal fluid (CSF) pressure may be analyzed to monitor the heart rate and breathing rate of patient 12C. A clinician initiates a CSF pressure sensor to being monitoring heart rate and/or breathing rate (138). Alternatively, the CSF pressure sensor may be implanted within the brain or spinal cord of patient 12C to acquire accurate pressure signals. The CSF pressure sensor must also store the pressure data or begin to transfer pressure data to an implanted or external device. As an example used herein, the CSF pressure sensor transmits signal data to an IMD 14.

Once the CSF pressure sensor is initiated, the CSF pressure sensor measures CSF pressure and transmits the data to an IMD 14 (140). An IMD 14 analyzes the CSF pressure signal to identify the heart rate (142) and breathing rate (144) of patient 12C. The heart rate and breathing rate can be identified within the overall CSF pressure signal. Higher frequency fluctuations (e.g. 40 to 150 beats per minute) can be identified as the heart rate while lower frequency fluctuations (e.g. 3 to 20 breaths per minute) in CSF pressure are the breathing rate. An IMD 14 may employ filters, transformations, or other signal processing techniques to identify the heart rate and breathing rate from the CSF pressure signal.

An IMD 14 may utilize the heart rate and breathing rate information as additional information when determining the sleep quality metric of patient 12C (146). For example, faster heart rates and faster breathing rates may indicate that patient 12C is not sleeping. An IMD 14 may then store the sleep quality metric or use it to adjust stimulation therapy (148). In addition, to the sleep quality metric, an IMD 14 may use heart rate and breathing rate information to determine an activity metric that is stored for review or used in therapy.

Various embodiments of the invention have been described. However one skilled in the art will appreciate that various modifications may be made to the described embodiments without departing from the scope of the invention. For example, although described herein primarily in the context of treatment with an implantable neurostimulator or implantable pump, the invention is not so limited. Moreover, the invention is not limited to implantable medical devices. The invention may be embodied in any implantable or external medical device that delivers therapy to treat any ailment of symptom of a patient.

As discussed above, the ability of a patient to experience quality sleep, e.g., the extent to which the patient able to achieve adequate periods of undisturbed sleep in deeper, more restful sleep states, may be negatively impacted by any of a variety of ailments or symptoms. Accordingly, the sleep quality of a patient may reflect the progression, status, or severity of the ailment or symptom. Further, the sleep quality of the patient may reflect the efficacy of a particular therapy or therapy parameter set in treating the ailment or symptom. In other words, it may generally be the case that the more efficacious a therapy or therapy parameter set is, the higher quality of sleep the patient will experience.

As discussed above, in accordance with the invention, sleep quality metrics may be monitored, and used to control delivery of a therapy for the ailment or symptom. In this manner, embodiments of the invention may provide therapy that is response to the progression or status of the ailment or symptom. As an example, chronic pain may cause a patient to have difficulty falling asleep, experience arousals during sleep, or have difficulty experiencing deeper sleep states. Systems according to the invention may monitor sleep quality metrics to provide therapy that addresses changes in the extent to which the patient is experiencing pain. In some embodiments, systems according to the invention may include any of a variety of medical devices that deliver any of a variety of therapies to treat chronic pain, such as SCS, DBS, cranial nerve stimulation, peripheral nerve stimulation, or one or more drugs. Systems may use the techniques of the invention described above to determine sleep quality metrics for the patient control delivery of such therapies, e.g., by modifying an intensity of the therapy or changing a therapy parameter set.

As another example, psychological disorders may cause a patient to experience low sleep quality. Accordingly, embodiments of the invention may determine sleep quality metrics to track the status or progression of a psychological disorder, such as depression, mania, bipolar disorder, or obsessive-compulsive disorder. Further, systems according to the invention may include any of a variety of medical devices that deliver any of a variety of therapies to treat a psychological disorder, such as DBS, cranial nerve stimulation, peripheral nerve stimulation, vagal nerve stimulation, or one or more drugs. Systems may use the techniques of the invention described above to control such therapies based on sleep quality metrics to, for example, provide responsive therapy that addresses changes in the progression or status of such psychological disorders.

Movement disorders, such as tremor, Parkinson's disease, multiple sclerosis, or spasticity, may also affect the sleep quality experienced by a patient. The uncontrolled movements, e.g., tremor or shaking, associated such disorders, particularly in the limbs, may cause a patient to experience disturbed sleep. Accordingly, systems according to the invention may monitor sleep quality metrics to determine the state or progression of a movement disorder.

Further, systems according to the invention may include any of a variety of medical devices that deliver any of a variety of therapies to treat a movement disorders, such as DBS, cortical stimulation, or one or more drugs. Baclofen, which may or may not be intrathecally delivered, is an example of a drug that may be delivered to treat movement disorders. Systems may use the techniques of the invention described above to control delivery of such therapies based sleep quality metric values. In this manner, such systems may provide therapy that is responsive to changes in the intensity or severity of the movement disorders. Movement disorders, psychological disorders, and other disorders treated with deep brain stimulation may be more generally referred to as neurological disorders or non-respiratory neurological disorders. As described herein, the disclosure is directed to controlling the delivery of therapy to treat such neurological disorders.

These and other embodiments are within the scope of the following claims.

The invention claimed is:

1. A method comprising:
monitoring at least one physiological parameter of a patient via a medical device that delivers at least one of a movement disorder therapy, psychological disorder therapy, or deep brain stimulation to a patient;
determining a value of a metric that is indicative of sleep quality based on the at least one physiological parameter; and
automatically controlling delivery of the at least one of the movement disorder therapy, psychological disorder therapy, or deep brain stimulation by the medical device based on the sleep quality metric value.

2. The method of claim 1, wherein the sleep quality metric comprises sleep efficiency, and determining the value of the sleep quality metric comprises:
identifying when the patient is attempting to sleep;
identifying when the patient is asleep; and
determining a percentage of time that the patient is asleep while the patient is attempting to sleep.

3. The method of claim 1, wherein the sleep quality metric comprises sleep latency, and determining the value of the sleep quality metric comprises:
identifying a first time when the patient begins attempting to sleep;
identifying a second time when the patient falls asleep; and
determining an amount of time between the first and second times.

4. The method of claim 1, wherein determining the value of the sleep quality metric comprises:
identifying when the patient is within a sleep state; and
determining an amount of time that the patient was within the sleep state.

5. The method of claim 4, wherein the sleep state comprises at least one of an S3 sleep state and an S4 sleep state.

6. The method of claim 4, wherein identifying when the patient is within a sleep state comprises:
monitoring a frequency of an electroencephalogram (EEG) signal of the patient; and
identifying the sleep state based on the frequency.

7. The method of claim 1, wherein controlling delivery of the therapy comprises:
comparing the sleep quality metric value to a threshold value; and
adjusting the therapy based on the comparison.

8. The method of claim 7, wherein adjusting the therapy comprises adjusting the therapy in an amount proportional to at least one of a difference and a ratio between the sleep quality metric value and the threshold value.

9. The method of claim 7, wherein adjusting the therapy comprises increasing the intensity of the therapy at a first rate and decreasing the intensity of the therapy at a second rate.

10. The method of claim 1, further comprising:
determining a plurality of values of the sleep quality metric over time;
associating each of the determined values of the sleep quality metric with a current therapy parameter set; and
for each of a plurality of therapy parameter sets, determining a representative value of the sleep quality metric based on the values of the sleep quality metric associated with the therapy parameter set, and
wherein controlling the therapy comprises automatically selecting one of the therapy parameter sets for delivery of the therapy based on the representative sleep quality metric values for the therapy parameter sets.

11. The method of claim 1, wherein automatically controlling delivery of the at least one of the movement disorder therapy, psychological disorder therapy, or deep brain stimulation comprises automatically controlling delivery of deep brain stimulation by the medical device based on the sleep quality metric value.

12. A medical device comprising:
a therapy module to deliver at least one of a movement disorder therapy, psychological disorder therapy, or deep brain stimulation to a patient; and
a processor to monitor at least one physiological parameter of a patient based on at least one signal received from at least one sensor, determine a value of a metric that is indicative of sleep quality based on the at least one physiological parameter, and control delivery of the at least one of the movement disorder therapy, psychological disorder therapy, or deep brain stimulation by the therapy module based on the sleep quality metric value.

13. The medical device of claim 12, wherein the sleep quality metric comprises sleep efficiency, and the processor identifies when the patient is attempting to sleep, identifies when the patient is asleep, and determines a percentage of time that the patient is asleep while the patient is attempting to sleep as the value of the sleep quality metric.

14. The medical device of claim 12, wherein the sleep quality metric comprises sleep latency, and the processor identifies a first time when the patient begins attempting to sleep, identifies a second time when the patient falls asleep, and determines an amount of time between the first and second times as the value of the sleep quality metric.

15. The medical device of claim 12, wherein the processor identifies when the patient is within a sleep state, and determines an amount of time that the patient was within the sleep state as the value of the sleep quality metric.

16. The medical device of claim 15, wherein the sleep state comprises at least one of an S3 sleep state and an S4 sleep state.

17. The medical device of claim 12, further comprising an electroencephalogram (EEG) module that monitors a frequency of an EEG signal of the patient, wherein the EEG module identifies the sleep state based on the frequency.

18. The medical device of claim 12, wherein the processor compares the sleep quality metric value to a threshold value, and adjusts the therapy based on the comparison.

19. The medical device of claim 18, wherein the processor adjusts the therapy in an amount proportional to at least one of a difference and a ratio between the sleep quality metric value and the threshold value.

20. The medical device of claim 18, wherein the processor increases the intensity of the therapy at a first rate and decreases the intensity of the therapy at a second rate.

21. The medical device of claim 11,
further comprising a memory to store information identifying a plurality of therapy parameter sets,
wherein the processor determines a plurality of values of the sleep quality metric over time, and associates each of the determined values of the sleep quality metric with a current one of the therapy parameter sets,
wherein, for each of the therapy parameter sets, the processor determines a representative value of the sleep quality metric based on the values of the sleep quality metric associated with the therapy parameter set, and stores the representative value of the sleep quality metric in association with the therapy parameter set within the memory, and
wherein the processor automatically selects one of the therapy parameter sets for delivery of the therapy based on the representative sleep quality metric values for the therapy parameter sets.

22. A computer-readable medium comprising instructions that cause a programmable processor to:
monitor at least one physiological parameter of a patient via a medical device delivers at least one of a movement disorder therapy, psychological disorder therapy, or deep brain stimulation to the patient;
determine a value of a metric that is indicative of sleep quality based on the at least one physiological parameter; and
control delivery of the at least one of the movement disorder therapy, psychological disorder therapy, or deep brain stimulation by the medical device based on the sleep quality metric value.

23. The medical device of claim 22, wherein the therapy module delivers deep brain stimulation, and the processor controls delivery of the deep brain stimulation by the therapy module based on the sleep quality metric value.

24. The computer-readable medium of claim 1, wherein the instructions that cause the programmable processor to control delivery of the at least one of the movement disorder therapy, psychological disorder therapy, or deep brain stimulation by the medical device based on the sleep quality metric value cause the programmable processor to control the medical device to deliver deep brain stimulation based on the sleep quality metric value.

* * * * *